United States Patent [19]

Berneth et al.

[11] Patent Number: 5,118,814
[45] Date of Patent: Jun. 2, 1992

[54] TETRAINDOLYL-HEPTAMETHINE DERIVATIVES

[75] Inventors: Horst Berneth; Hubertus Psaar, both of Leverkusen; Günter Klug, Monheim, all of Fed. Rep. of Germany

[73] Assignee: Bayer Aktiengesellschaft, Leverkusen, Fed. Rep. of Germany

[21] Appl. No.: 414,060

[22] Filed: Sep. 28, 1989

[30] Foreign Application Priority Data

Oct. 6, 1988 [DE] Fed. Rep. of Germany ....... 3833997

[51] Int. Cl.[5] .................. C07D 401/06; C07D 417/14; C07D 401/14
[52] U.S. Cl. .................. 548/455; 548/327; 548/336; 548/374; 548/379; 548/210; 544/32; 544/3; 544/143
[58] Field of Search ............... 548/455, 327, 336, 374, 548/379; 544/3, 32

[56] References Cited

U.S. PATENT DOCUMENTS

| | | | |
|---|---|---|---|
| 1,863,679 | 6/1932 | Wahl | 548/455 |
| 2,155,447 | 4/1939 | Roh | 548/455 |
| 3,850,913 | 11/1974 | Psaar | 548/455 |
| 3,855,209 | 12/1974 | Hoyle | 548/455 |
| 3,916,069 | 10/1975 | Tiers et al. | 548/455 |
| 4,102,893 | 7/1978 | Garner et al. | 548/456 |

FOREIGN PATENT DOCUMENTS

| | | |
|---|---|---|
| 1248193 | 8/1967 | Fed. Rep. of Germany . |
| 2257711 | 5/1973 | Fed. Rep. of Germany . |
| 2265233 | 2/1977 | Fed. Rep. of Germany . |
| 2951353 | 7/1981 | Fed. Rep. of Germany . |

OTHER PUBLICATIONS

Chemical Abstracts, vol. 107, No. 13, Sep. 18, 1987, Columbus, Ohio, U.S.A. Banerji, J. et al., "Electrophilic substitution of indoles. Part IX. Reaction of indoles with ininium systems", p. 615, col. 1, para. No. 115 454w & Indian J. Chem., Sect. B 1986, 25B(12), 1204-1208.
Chemical Abstracts, vol. 101, No. 24, Dec. 10, 1984, Columbus, Ohio, U.S.A. Konyukhova, T. M. et al. "3,3-Bis(3-indolyl)phthalides and their properties", p. 66, col. 2, para. No. 212 655w & Zh. Vses. Khim. O-va-.im. D. I. Mendeleeva 1984, 29(4), 467-468.
Chemical Abstracts, vol. 89,No. 13, Sep. 25, 1978, Columbus, Ohio, U.S.A. Berti, C. et al., "Synthesis and reactivity of indolylmethyl cations", p. 872, col. 2, para. No. 109 002r & J. Heterocycl. Chem. 1978, 15(3), 433-437.
Chemical Abstracts, vol 70, No. 22, Jun. 2,1969, Columbus, Ohio, U.S.A. Lin, Chao-Han "3,3-Bis(indol-3-yl)phthalides " p. 74, col. 1, para. No. 97 960u & S. African 68 00,323.
Chemical Abstracts, vol. 93, No. 5, Aug. 4, 1980, Columbus, Ohio, U.S.A. Volovel'Skii, L. N. et al. "Indole derivatives of steroid ketones" p. 966, col. 2, para. No. 46 967u & Zh. Obshch. Khim. 1980, 50(1), 190-195.

Primary Examiner—David B. Springer
Attorney, Agent, or Firm—Sprung Horn Kramer & Woods

[57] ABSTRACT

Tetraindolyl-heptamethine derivatives of the isomeric formulae

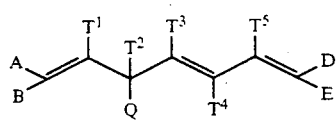

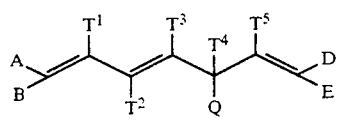

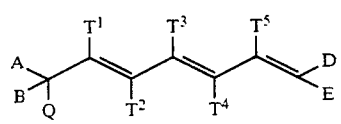

and

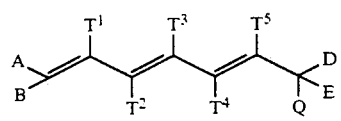

in which A, B, D and E denote

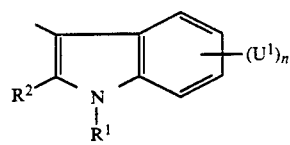

and may be identical to or different from one another, and the other symbols have the meaning indicated in the description, are used in pressure-sensitive and heat-sensitive recording materials.

4 Claims, No Drawings

TETRAINDOLYL-HEPTAMETHINE DERIVATIVES

The invention relates to tetraindolyl-heptamethine derivatives of the isomeric formulae

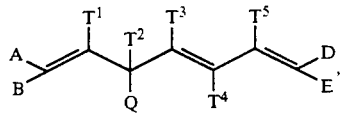 (I)

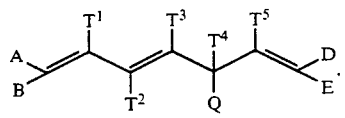 (II)

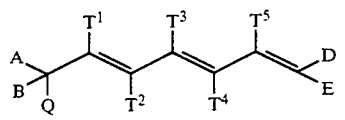 (III)

and

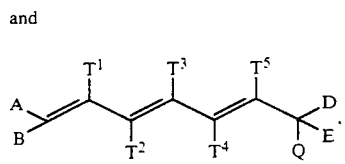 (IV)

in which A, B, D and E denote

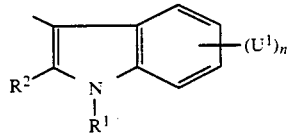

and may be identical to or different from one another,

Q denotes $NV^1V^2$, SW, $SO_2X$ or $CLY^1Y^2$, $R^1$ denotes hydrogen, alkyl, alkenyl, cycloalkyl, aralkyl or a heterocyclic radical bonded via alkyl, $R^2$ denotes hydrogen, alkyl, alkenyl, cycloalkyl, aralkyl, aryl or a heterocyclic radical optionally bonded via alkyl, $T^1$ to $T^5$ denote hydrogen, alkyl, alkenyl, cycloalkyl, aralkyl, halogen, alkoxy, dialkylamino, cyano, hydroxycarbonyl-, alkoxycarbonyl, aryl or a heterocyclic radical optionally bonded via alkyl, or in each case two of the radicals $T^1$ to $T^5$ denote the missing members of a five- to seven-membered ring which may be aromatic or partially hydrogenated and may contain up to 2 hetero atoms from the series comprising O, N or S, $U^1$ denotes hydrogen, alkyl, alkenyl, cycloalkyl, aralkyl, aryl, hydroxyl, alkoxy, halogen, dialkylamino, nitro, cyano, alkylthio, alkoxycarbonyl, dialkylaminocarbonyl, alkoxycarbonyloxy or alkylsulphonyl, or together with $R^1$ denotes a $C_2$ or $C_3$ bridge, $V^1$ and $V^2$ independently of one another denote hydrogen, alkyl, alkenyl, cycloalkyl, aryl or heterocyclic radicals optionally bonded via alkyl, $—CO—Z^1$,

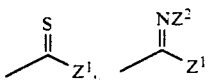

or CN, or together with the nitrogen atom denote an optionally completely or partially hydrogenated ring containing 0-3 hetero atoms from the series comprising O, N, S, $SO_2$, W denotes hydrogen, alkyl, alkenyl, cycloalkyl, aryl or heterocyclic radicals optionally bonded via alkyl,

or CN,

X denotes alkyl, alkenyl, cycloalkyl or aryl or heterocyclic radicals optionally bonded via alkyl, L denotes hydrogen, alkyl, alkenyl, cycloalkyl, halogen, aryl or heterocyclic radicals bonded via alkyl, or has the meaning of $Y^1$ or $Y^2$, $Y^1$ and $Y^2$ denote $—CO-Z^1$,

$—CN$, $—SO_2—Z^1$, $NO_2$, aryl or a heterocyclic radical, $Z^1$ to $Z^3$ denote hydrogen, alkyl, alkenyl, cycloalkyl, alkoxy, alkylthio, cycloalkoxy, amino, mono- or bisalkylamino, arylamino or aryl or heterocyclic radicals optionally bonded via alkyl or alkoxy, or $Z^1$ and $Z^2$ together with $V^1$ or $V^2$ or $Y^1$ or $Y^2$ or another radical $Z^1$ or $Z^2$ denote the missing members of an optionally completely or partially hydrogenated ring containing 0-2 hetero atoms from the series comprising O, N, S or $SO_2$, which is optionally fused to benzene, where $Z^{1'}$ and $Z^{2'}$ have the meaning of $Z^1$ and $Z^2$, and n denotes 1 or 2 and all cyclic and non-cyclic radicals may carry non-ionic substituents customary in dyestuff chemistry, their preparation and use in pressure-sensitive and heat-sensitive recording materials which can be read in the 750-950 nm infrared region, and recording materials which contain these compounds.

Alkyl radicals, including those in, for example, alkoxy, alkylamino or aralkyl, may have up to 18 C atoms and may be substituted, for example, by halogen, alkoxy, nitro, cyano, alkoxycarbonyl- or alkylsulphonyl.

Alkenyl radicals may have up to 18 C atoms and may be substituted, for example, by halogen, alkoxy, cyano or alkoxycarbonyl.

Cycloalkyl radicals may have 3-8 C atoms and may be substituted, for example, by alkyl, alkoxy, halogen, cyano, alkoxycarbonyl or aryl.

Aryl radicals, including those in aralkyl groups, are phenyl, naphthyl or anthracenyl which may be substituted, for example, by alkyl, alkoxy, halogen, cyano, alkoxycarbonyl, nitro, aryl or heterocyclic radicals, where up to 5 substituents, which do not have to be identical, are possible.

Heterocyclic radicals, including those which are bonded via alkyl, are five- to seven-membered aromatic or quasi-aromatic heterocycles or their partially or completely hydrogenated derivatives which contain O, N, S or $SO_2$ as hetero atoms, where a maximum of 4 such hetero atoms, which may also be mixed with one another, occur in a ring, and where these heterocycles are fused to benzene, naphthalene or pyridine and/or may be substituted by alkyl, alkoxy, halogen, cyano, alkoxycarbonyl, nitro or aryl.

Preferred tetraindolylheptamethine derivatives are those of the isomeric formulae

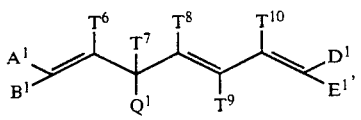
(V)

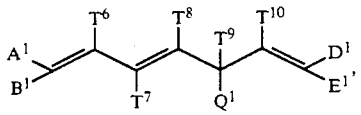
(VI)

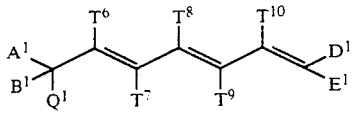
(VII)

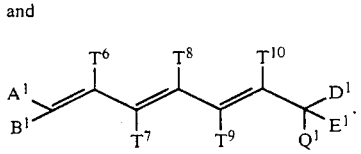
(VIII)

in which $A^1$, $B^1$, $D^1$ and $E^1$ denote

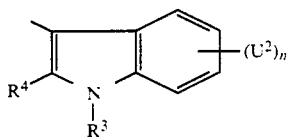

and may be identical to or different from one another. $Q^1$ denotes

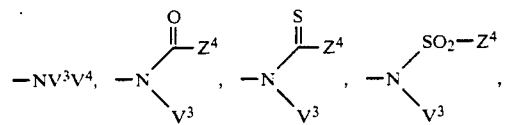

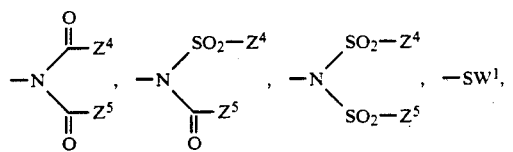

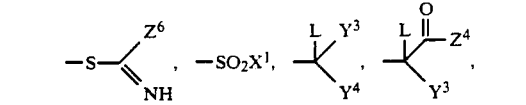

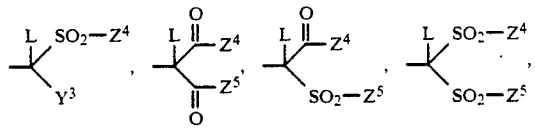

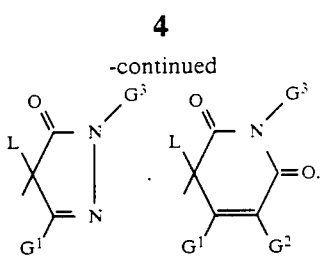

$R^3$ denotes hydrogen, $C_1$–$C_{18}$-alkyl may be substituted by chlorine, $C_1$–$C_4$-alkoxy, cyano or $C_1$–$C_4$-alkoxycarbonyl, or allyl, cyclopentyl or cyclohexyl, or benzyl, phenethyl, naphthylmethyl or picolyl radicals optionally substituted by $C_1$–$C_4$-alkyl, chlorine and/or $C_1$–$C_4$-alkoxy, $R^4$ denotes hydrogen, $C_1$–$C_{18}$-alkyl which may be substituted by chlorine, $C_1$–$C_4$-alkoxy, cyano or $C_1$–$C_4$-alkoxycarbonyl, or allyl, cyclopentyl or cyclohexyl, or benzyl, phenethyl, naphthylmethyl, picolyl, quinolylmethyl, phenyl, naphthyl, pyridyl, pyrimidyl, pyrazinyl, imidazolyl, oxazolyl, thiazolyl, triazolyl, benzimidazolyl, benzoxazolyl, benzothiazolyl or quinolyl radicals optionally substituted by $C_1$–$C_4$-alkyl, chlorine, bromine, $C_1$–$C_4$-alkoxy, cyano, nitro and/or $C_1$–$C_4$-alkoxycarbonyl, $T^6$–$T^{10}$ denote hydrogen, $C_1$–$C_8$-alkyl which may be substituted by chlorine, $C_1$–$C_4$-alkoxy, cyano or $C_1$–$C_4$-alkoxycarbonyl, or vinyl, allyl, cyclopentyl, cyclohexyl, fluorine, chlorine, bromine, $C_1$–$C_8$-alkoxy which may be further substituted by $C_1$–$C_4$-alkoxy, or $C_1$–$C_4$-dialkylamino, piperidino, pyrrolidino, nitro, cyano, $C_1$–$C_4$-alkoxycarbonyl, or benzyl, phenethyl, naphthylmethyl, picolyl, phenyl, naphthyl, pyridyl, quinolyl, pyrimidyl, pyrazinyl, indolyl, indolenyl, indolizinyl, imidazolyl, oxazolyl, thiazolyl, triazolyl, benzimidazolyl, benzoxazolyl or benzothiazolyl radicals optionally substituted by $C_1$–$C_4$-alkyl, chlorine, $C_1$–$C_4$-alkoxy, $C_1$–$C_4$-alkylsulphonyl, cyano and/or $C_1$–$C_4$-alkoxycarbonyl, or in each case two of the radicals $T^5$ to $T^{10}$ denote a bridge of the formulae

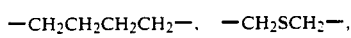
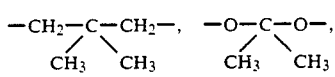
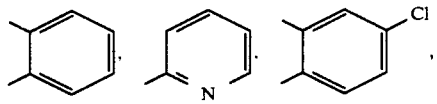

$U^2$ denotes hydrogen, $C_1$–$C_8$-alkyl, allyl, cyclohexyl, benzyl, phenyl, hydroxyl, $C_1$–$C_4$-alkoxy, chlorine, bromine, $C_1$–$C_4$-dialkylamino, nitro, cyano, $C_1$–$C_4$-alkylthio, $C_1$–$C_4$-alkoxycarbonyl, $C_1$–$C_4$-dialkylaminocarbonyl, $C_1$–$C_4$-alkoxycarbonyloxy or $C_1$–$C_4$-alkylsulphonyl or together with $R^3$ denotes a —$CH_2CH_2$— or —$CH_2CH_2CH_2$— bridge which may be substituted by a maximum of three methyl groups, $V^3$, $V^4$ and $W^1$ independently of one another denote hydrogen, $C_1$–$C_{18}$-alkyl which may be substituted by chlorine, $C_1$-$C_4$-alkoxy, cyano or $C_1$-$C_4$-alkoxycarbonyl, or allyl, cyclopentyl, cyclohexyl or cyano, or benzyl, phenethyl, naphthylmethyl, picolyl, quinolylmethyl, phenyl, naphthy, pyridyl, pyrimidyl, pyrazinyl, imidazolyl, oxazolyl, thiazolyl, triazolyl, benzimidazolyl, benzoxazolyl, benzothiazolyl, quinolyl, tetrahydrothiophene dioxide-3-yl, piperidin-4-yl or piperazin-1-yl-ethyl radicals optionally substituted by $C_1$-$C_4$-alkyl, chlorine, bromine, $C_1$-$C_4$-alkoxy, cyano, nitro or $C_1$-$C_4$-alkoxycarbonyl, or $V^3$ and $V^4$ together with the nitrogen denote pyrrolidine, piperidine, piperazine, morpholine, pyrazoline, pyrazole, imidazole, triazole or tetrazole radicals optionally substituted by $C_1$-$C_4$-alkyl, chlorine, $C_1$-$C_4$-alkoxy or phenyl, $X^1$ denotes $C_1$-$C_{18}$-alkyl which may be substituted by chlorine, $C_1$-$C_4$-alkoxy, cyano or $C_1$-$C_4$-alkoxycarbonyl, or allyl, cyclopentyl or cyclohexyl, or benzyl, phenethyl, naphthylmethyl, picolyl, quinolylmethyl, phenyl, naphthyl, pyridyl, pyrimidyl, pyrazinyl, imidazolyl, oxazolyl, thiazolyl, triazolyl, benzimidazolyl, benzoxazolyl, benzothiazolyl or quinolyl radicals optionally substituted by $C_1$-$C_4$-alkyl, chlorine, bromine, $C_1$-$C_4$-alkoxy, cyano, nitro or $C_1$-$C_4$-alkoxycarbonyl, L denotes hydrogen, $C_1$-$C_8$-alkyl which may be substituted by chlorine, $C_1$-$C_4$-alkoxy, cyano or $C_1$-$C_4$-alkoxycarbonyl, or allyl, cyclopentyl, cyclohexyl, chlorine, cyano or $C_1$-$C_8$-alkoxycarbonyl, or benzyl, phenethyl, picolyl, phenyl, naphthyl or pyridyl radicals optionally substituted by $C_1$-$C_4$-alkyl, chlorine, $C_1$-$C_4$-alkoxy, cyano, nitro or $C_1$-$C_4$-alkoxycarbonyl, $Y^3$ and $Y^4$ denote cyano, nitro or phenyl, naphthyl, pyridyl, pyrimidyl, pyrazinyl, imidazolyl, oxazolyl, thiazolyl, triazolyl, benzimidazolyl, benzoxazolyl, benzothiazolyl or quinolyl radicals optionally substituted by $C_1$-$C_4$-alkyl, chlorine, bromine, $C_1$-$C_4$-alkoxy, cyano, nitro, $C_1$-$C_4$-alkylsulphonyl or $C_1$-$C_4$-alkoxycarbonyl, $Z^4$, $Z^5$ and $Z^6$ independently of one another denote hydrogen, $C_1$-$C_{18}$-alkyl which may be substituted by chlorine, $C_1$-$C_4$-alkoxy, cyano or $C_1$-$C_4$-alkoxycarbonyl, or allyl, cyclopentyl, cyclohexyl, $C_1$-$C_{18}$-alkoxy, $C_1$-$C_{18}$-alkylthio, cyclopentoxy, cyclohexoxy, amino or mono- or bis-$C_1$-$C_{12}$-alkylamino, or anilino, N-$C_1$-$C_4$-alkylanilino, diphenylamino, benzyl, benzyloxy, benzylamino, N-$C_1$-$C_4$-alkylbenzylamino, dibenzylamino, phenethyl, phenethoxy, phenethamino, pyridylethoxy, pyridylamino, picolyl, phenyl, naphthyl, pyridyl, pyrimidyl, pyrazinyl, imidazolyl, oxazolyl, thiazolyl, triazolyl, benzimidazolyl, benzoxazolyl, benzothiazolyl, quinolyl or piperazin-1-yl-ethyl radicals optionally substituted by $C_1$-$C_4$-alkyl, chlorine, bromine, $C_1$-$C_4$-alkoxy, cyano, nitro or $C_1$-$C_4$-alkoxycarbonyl, or $Z^4$ together with $Z^5$ or $V^3$ or $Y^3$ denote a bridge of the formulae

—CH$_2$CH$_2$—, —CH=CH—, —CH$_2$CH$_2$CH$_2$—

—CH$_2$CH$_2$CH$_2$CH$_2$—, 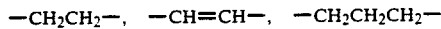

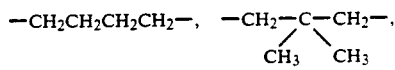, —CH=CH—CH$_2$—.

—CH=CH—CH=CH—. 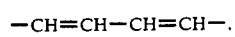, 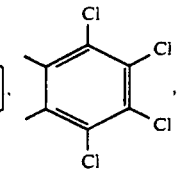,

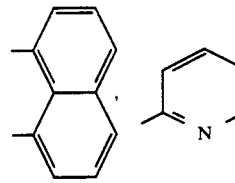 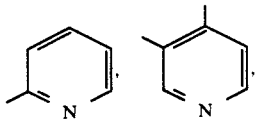

$G^1$ and $G^2$ independently of one another denote hydrogen, $C_1$-$C_8$-alkyl which may be substituted by chlorine, $C_1$-$C_4$-alkoxy, cyano, or $C_1$-$C_4$-alkoxycarbonyl, or allyl, cyclopentyl, cyclohexyl, hydroxyl, chlorine, $C_1$-$C_8$-alkoxy. cyano, $C_1$-$C_8$-alkoxycarbonyl, nitro or $C_1$-$C_8$-alkylsulphonyl, or benzyl, phenethyl, picolyl, phenyl, naphthyl, pyridyl, imidazolyl, oxazolyl, thiazolyl, triazolyl, benzimidazolyl, benzothiazolyl or benzoxazolyl radicals optionally substituted by $C_1$-$C_4$-alkyl, chlorine, $C_1$-$C_4$-alkoxy, cyano, nitro or $C_1$-$C_4$-alkoxycarbonyl, $G^3$ denotes hydrogen, $C_1$-$C_8$-alkyl which may be substituted by chlorine, $C_1$-$C_4$-alkoxy, cyano or $C_1$-$C_4$-alkoxycarbonyl, or allyl, cyclopentyl or cyclohexyl, or benzyl, phenethyl, picolyl, phenyl, naphthyl or pyridyl radicals optionally substituted by $C_1$-$C_4$-alkyl, chlorine, $C_1$-$C_4$-alkoxy, cyano, nitro or $C_1$-$C_4$-alkoxycarbonyl, and n denotes 1 or 2.

Particularly preferred tetraindolylheptamethine derivatives are those of the formula V to VIII, in which $Q^1$ denotes $C_1$-$C_8$-mono- or dialkylamino, or pyrrolidino, piperidino, morpholino, piperazino, hydroxyethylpiperazino, pyrazolo, imidazolo, triazolo or tetrazolo radicals optionally substituted by methyl, chlorine or methoxy, or anilino, N-$C_1$-$C_4$-alkylanilino, diphenylamino, benzylamino, N-$C_1$-$C_4$-alkyl-N-benzylamino, pyridylamino, benzoylamino, N-$C_1$-$C_4$-alkylbenzoylamino, N-phenylbenzoylamino, benzenesulphonylamino, N-$C_1$-$C_4$-alkylbenzenesulphonylamino, phthalimido, naphthalimido, homophthalimido, benzoyl-2-sulphonylimido, succinimido or maleimido radicals optionally substituted by methyl, ethyl, chlorine, cyano or nitro, or aminocarbonylamino, $C_1$-$C_8$-alkoxycarbonylamino or $C_1$-$C_8$-alkylthio, or phenylthio,

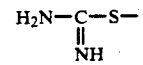

or $C_1$-$C_8$-alkylsulphonyl optionally substituted by methyl, chlorine or methoxy, phenylsulphonyl, benzylsulphonyl or naphthylsulphonyl optionally substituted by methyl, ethyl, chlorine, bromine, cyano or methoxycarbonyl, or benzyl, naphthylmethyl, picolyl, quinolylmethyl, imidazolylmethyl, benzimidazolylmethyl, oxazolylmethyl, benzoxazolylmethyl, thiazolylmethyl, benzothiazolylmethyl, triazolylmethyl or tetrazolylmethyl radicals substituted in the α-position by cyano, $C_1$-$C_4$-alkoxycarbonyl, $C_1$-$C_4$-alkylsulphonyl, $C_1$-$C_4$-alkanoyl or benzoyl and optionally furthermore substituted by methyl, ethyl, chlorine, bromine, cyano, nitro or methoxycarbonyl, or dicyanomethyl, cyano-$C_1$-$C_4$-alkoxycarbonylmethyl, bis-$C_1$-$C_4$-alkoxycarbonylmethyl, cyano-$C_1$-$C_4$-alkanoylmethyl or bis-$C_1$-$C_4$-alkanoylmethyl, or cyano-benzoylmethyl, $C_1$-$C_4$-alkanoylbenzoylmethyl, $C_1$-$C_4$-alkoxycarbonyl-benzoylmethyl, dibenzoylmethyl, cyano-phenylsulphonylmethyl, $C_1$-$C_4$-alkanoyl-phenylsulphonylmethyl, $C_1$-$C_4$-alkoxycarbonyl-phenylsulphonylmethyl or bis-phenylsulphonylmethyl radicals optionally substituted by methyl, ethyl, chlorine, cyano, nitro or methoxycarbonyl, or the radicals of 1,3-cyclopentanedione, 1,3-cyclohexanedione, 1,3-indanedione, Meldrum,s acid, pyrazolone, 2-hydroxy-6-pyridone or barbituric acid optionally substituted by methyl, ethyl, chlorine, methoxy, ethoxy, phenyl, cyano, methoxycarbonyl or ethoxycarbonyl, $R^3$ denotes hydrogen, $C_1$-$C_8$-alkyl which may be substituted by chlorine, methoxy, ethoxy, cyano or methoxycarbonyl, or allyl, cyclopentyl or cyclohexyl, or benzyl, phenethyl or picolyl radicals optionally substituted by methyl, chlorine or methoxy, $R^4$ denotes hydrogen, $C_1$-$C_8$-alkyl which may be substituted by chlorine, methoxy, ethoxy, cyano or methoxycarbonyl, or allyl, cyclopentyl or cyclohexyl, or benzyl, phenethyl, picolyl, phenyl, naphthyl, pyridyl, pyrimidyl, benzimidazolyl, benzoxazolyl, benzothiazolyl or quinolyl radicals optionally substituted by methyl, chlorine, methoxy, cyano, nitro and/or methoxycarbonyl, $T^6$ and $T^{10}$ denote hydrogen, $C_1$-$C_8$-alkyl which may be substituted by chlorine, methoxy, cyano or methoxycarbonyl, or vinyl, allyl, cyclopentyl, cyclohexyl, chlorine, $C_1$-$C_8$-alkoxy, cyano, methoxycarbonyl, nitro or benzyl, or phenyl or pyridyl radicals optionally substituted by methyl, chlorine, cyano or methoxy, $T^7$ to $T^9$ denote hydrogen, $C_1$-$C_8$-alkyl which may be substituted by chlorine, methoxy, cyano or methoxycarbonyl, or allyl, cyclopentyl, cyclohexyl, chlorine, bromine, cyano, methoxycarbonyl or ethoxycarbonyl, nitro, $C_1$-$C_4$-alkoxy, $C_1$-$C_4$-dialkylamino or benzyl, or phenyl, naphthyl, pyridyl, quinolyl, pyrimidyl, indolenyl, indolizinyl, imidazolyl, oxazolyl, thiazolyl, benzimidazolyl-, benzoxazolyl or benzothiazolyl radicals optionally substituted by methyl, ethyl, chlorine, methoxy, ethoxy, cyano, nitro and/or methoxycarbonyl, or $T^7$ together with $T^8$ or $T^9$ or $T^8$ together with $T^9$ denote a bridge of the formulae

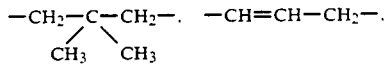

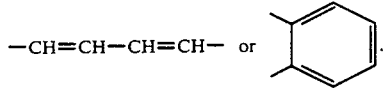

$U^2$ denotes hydrogen, $C_1$-$C_4$-alkyl, cyclohexyl, benzyl, $C_1$-$C_4$-alkoxy, chlorine, $C_1$-$C_4$-dialkylamino, nitro, cyano, methoxycarbonyl or ethoxycarbonyl or methylsulphonyl, where $U^2$ may be in the 5-, 6- and/or 7-position of the indolyl radical, or a radical $U^2$ in the 7-position together with $R^3$ can form a bridge of the formulae

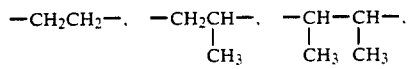

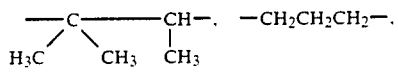

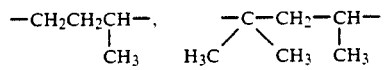

and n denotes 1 or 2.

Very particularly preferred tetraindolylheptamethine derivatives are those of the formula

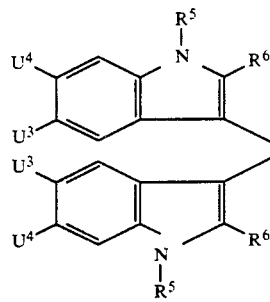

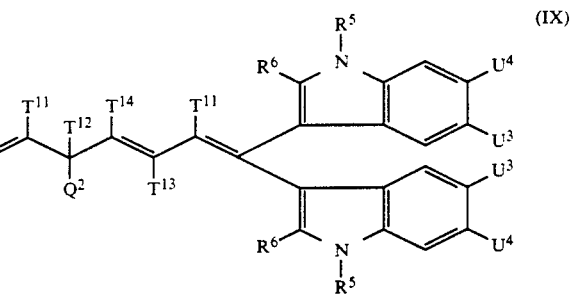

(IX)

and their isomeric forms with reference to the position of the $Q^2$ group, as are reproduced in the formulae II to IV and VI to VIII, in which $Q^2$ denotes dimethylamino, diethylamino, dipropylamino, dibutylamino, propylamino, butylamino, pyrrolidino, piperidino, morpholino, piperazino, pyrazolo, imidazolo, triazolo, anilino, 4-methylanilino, 4-chloroanilino, 4-methoxyanilino, 4-nitroanilino, N-methylanilino, benzylamino, N-methylbenzylamino, N-ethylbenzylamino, benzoylamino, benzenesulphonylamino, phthalimido, naphthalimido, succinimido, maleiimido, methylthio, ethylthio, phenylthio, methylsulphon-yl, ethylsulphonyl, propylsulphonyl, butylsulphonyl, hexylsulphonyl, octylsulphonyl, benzenesulphonyl, 4-methylbenzenesulphonyl, 4-chlorobenzenesulphonyl, α-cyanobenzyl, α-cyano-4-methylbenzyl, α-cyano-4-chlorobenzyl, α-cyano-4-nitrobenzyl, α-cyano-α-picolyl, α-cyano-γ-picolyl, dicyanomethyl, cyano-methoxycarbonylmethyl, cyano-ethoxycarbonylmethyl, bis-methoxycarbonylmethyl, bisethoxycarbonylmethyl, 1-cyanoaceton-1-yl, 1-cyanobutanon-1-yl, 1-methoxycarbonylaceton-1-yl, 1-ethoxycarbonylaceton-1-yl, 1,3-pentanedion-3-yl, 1-benzoylaceton-1-yl, 2-cyano-1-phenylethanon-2-yl, 2-methoxycarbonyl-1-phenylethanon-2-yl, dibenzoylmethyl, cyano-phenylsulphonylmethyl, bisphenylsulphonylmethyl, 1,3-cyclopentanedion-2-yl, 1,3-cyclohexanedion-2-yl, 5,5-dimethyl-1,3-cyclohexanedion-2-yl, 1,3-indanedion-2-yl, 2,2-dimethylperhydro-1,3-dioxine-4,6-dion-5-yl, 3-methyl-1-phenyl-2-pyrazolin-5-on-4-yl, 1-(2-chlorophenyl)-3-methyl-2-pyrazolin-5-on-4-yl, 3-methyl-1-(4-methylphenyl)-2-pyrazolin-5-on-4-yl, 3-methyl-1-(4-nitrophenyl)-2-pyrazolin-5-on-4-yl, 3-methyl-1-phenyl-5-imino-2-pyazolin-4-yl, 3-methyl-1-(3-sulpholanyl)-2-pyrazolin-5-on-4-yl, 3-ethoxycarbonyl-1-phenyl-2-pyrazolin-5-on-4-yl, 3-aminocarbonyl-1-phenyl-2-pyrazolin-5-on-4-yl, 4-hydroxy-1-m-ethyl-2(1H)-quinolinon-3-yl, 3-cyano-4-methyl-6-hydroxy-2(1H)pyridon-5-yl, 3-cyano-1,4-dimethyl-6-hydroxy-2(1H)-pyridon-5-yl, 2,4,6-(1H,3H,5H)-pyrimidine-trion-5-yl, $R^5$ denotes methyl, ethyl, propyl, butyl, hexyl, octyl, 2-cyanoethyl, 2-methoxyethyl, 2-methoxycarbonylethyl, 2-chloroethyl, 2-acetoxy-ethyl, cyclohexyl, allyl or benzyl $R^6$ denotes methyl, ethyl, propyl, butyl, hexyl, octyl, cyclohexyl, benzyl, phenyl, 2-, 3- or 4-chlorophenyl, 2-, 3- or 4-methox-yphenyl, 4-nitrophenyl, 2,4-dichlorophenyl, 2-, 3- or 4-tolyl or 2-, 3- or 4-pyridyl, $T^{11}$ denotes hydrogen, methyl, ethyl, propyl, butyl, vinyl, 2-chloroethyl, 2-cyanoethyl, chlorine, cyano, phenyl, 4-tolyl or 4-chlorophenyl, $T^{12}$ and $T^{13}$ denote hydrogen, methyl, ethyl, propyl, butyl, chlorine, cyano, methoxycarbonyl, dimethylamino, phenyl, 4-tolyl, 4-chlorophenyl or pyridyl or $T^{12}$ and $T^{13}$ together denote a grouping of the formulae

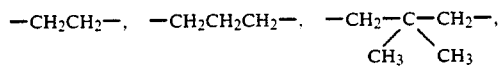

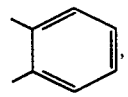, $T^{14}$ denotes hydrogen, methyl, ethyl, propyl, butyl, chlorine, bromine, cyano, phenyl, 4-tolyl, 4-chlorophenyl, 4-nitrophenyl, 4-pyridyl, 3,3-dimethyl-indolen-2-yl, indolizin-2-yl, 2-benzimidazolyl, 2-benzoxazolyl or 2-benzothiazolyl and $U^3$ and $U^4$ denote hydrogen, methyl, methoxy, chlorine, cyano, methoxycarbonyl or nitro.

The invention likewise relates to processes for the preparation of tetraindolylheptamethine derivatives of the formulae I to IV.

1. The preparation takes place by condensing ethenes of the formulae

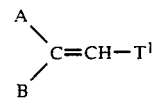 (X)

and/or

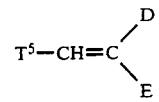 (XI)

or carbinols of the formulae

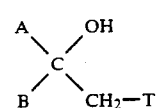 (XII)

and/or

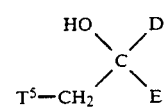 (XIII)

or salts of the formulae

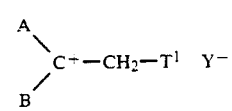 (XIV)

and/or

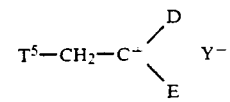 (XV)

with 1,3-dicarbonyl compounds of the formula

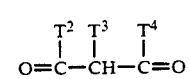 (XVI)

or their acetals or ketals of the formula

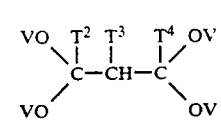 (XVII)

or vinylogous amidinium salts of the formula

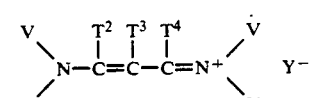 (XVIII)

or vinylogous chlorimmonium salts of the formulae

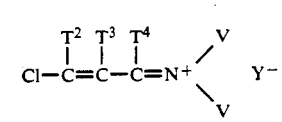 (XIX)

or

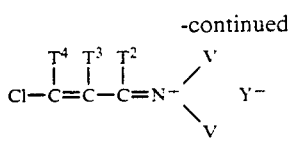 (XX)

and reaction with compounds of the formula

HQ   (XXI)

in which

A, B, D, E, Q and $T^1$ to $T^5$ have the abovementioned meaning and

V represents alkyl, aralkyl or aryl and $Y^-$ represents an anion.

The condensation is customarily carried out in solvents under acidic and/or basic conditions, it being possible to add a water- or alcohol-entraining agent, at temperatures between room temperature and the boiling point of the medium, preferably at 40°–140° C.

Suitable solvents are alcohols, such as methanol, ethanol, 1-propanol, 2-propanol, 1-butanol, 1-octanol, cyclohexanol or benzyl alcohol; or esters, such as methyl, ethyl or butyl acetate; chlorinated hydrocarbons, such as methylene chloride, ethylene chloride or chloroform; ketones, such as acetone or 2-butanone; aromatic compounds such as benzene, toluene or xylene; chlorinated aromatic compounds such as chlorobenzene or dichlorobenzene; carboxylic acids, such as formic acid, acetic acid or propionic acid; nitriles, such as acetonitrile or propionitrile; and anhydrides, such as acetic anhydride.

Suitable acids are inorganic acids, such as hydrochloric acid or sulphuric acid, tetrafluoboric acid, perchloric acid or phosphoric acid; carboxylic acids, such as formic acid, acetic acid or trifluoroacetic acid; sulphonic acids, such as methanesulphonic acid, ethanesulphonic acid, trifluoromethanesulphonic acid or nonafluorobutanesulphonic acid, benzenesulphonic acid or toluenesulphonic acid; phosphonic acids, such as methanephosphonic acid; or ion exchangers, such as those based on sulphonated styrene/divinylbenzene polymers.

Suitable bases are amines, such as triethylamine, triethanolamine, piperidine, pyrrolidine or pyridine Suitable water- or alcohol-entraining agents are anhydrides, such as acetic anhydride, trifluoroacetic anhydride or benzoic anhydride; acid chlorides, such as acetyl chloride, phosphorus oxychloride, thionyl chloride, oxalyl chloride or phosgene; or inorganic oxides, such as phosphorus pentoxide.

Examples of compounds of the formula XVI are:

O=CH—CH₂—CHO,

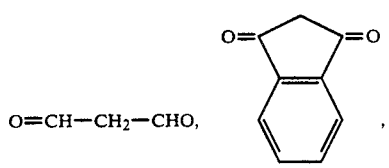

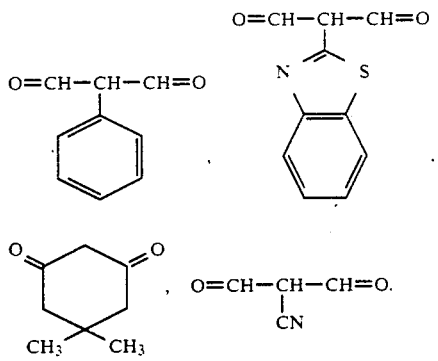

Examples of compounds of the formulae XVII are:

$(CH_3O)_2CH-CH_2-CH(OCH_3)_2$.

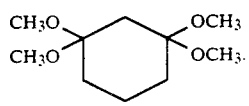

Examples of compounds of the formula XVIII are:

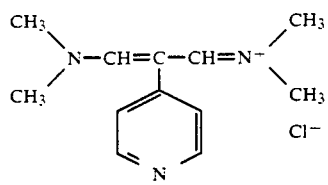

Examples of compounds of the formula XIX are:

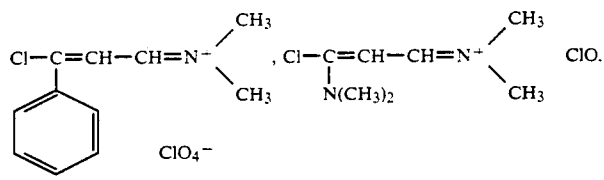

For the preparation of the derivatives of the formulae I–IV, this condensation mixture is either directly used further or diluted with solvents. A base is added after addition of the compound XXI. The temperatures are between room temperature and the boiling point of the medium, preferably between 20° and 140° C.

Solvents suitable for the dilution are alcohols, esters, ketones or nitriles as are described further above in more detail.

Suitable bases for the reaction with XXI are amines, such as triethylamine, triethanolamine, piperidine, pyrrolidine or pyridine; hydroxides, such as lithium hydroxide, sodium hydroxide, potassium hydroxide, calcium hydroxide or tetrabutylammonium hydroxide; carbonates, such as lithium carbonate, sodium carbonate, potassium carbonate or calcium carbonate; or alcoholates, such as lithium methylate, sodium methylate, sodium ethylate, sodium propylate, potassium methylate, potassium ethylate or sodium tert.-butylate; or ion exchangers, such as those based on amino-methylated styrenedivinylbenzene polymers.

2. The preparation is carried out by reacting tetraindolylheptamethine ethers or alcohols of the isomeric formulae

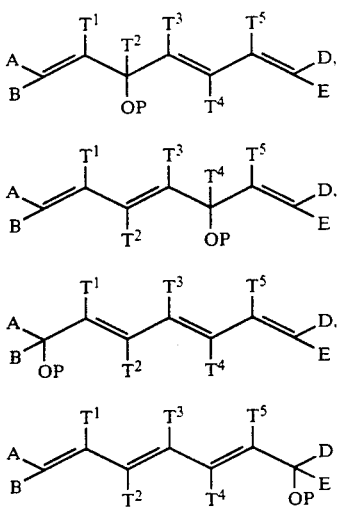

with HQ (XXI), in which

A, B, D, E, Q and $T^1$ to $T^5$ have the abovementioned meaning and

P denotes hydrogen, alkyl, alkenyl, cycloalkyl, aralkyl, aryl or a heterocyclic radical bonded via alkyl.

This reaction is carried out either in one step in the presence or absence of a solvent and in the presence or absence of an acidic catalyst or in two steps by reacting the ethers or alcohols of the formulae XXII–XXV with an acid to give the dyestuffs of the formula

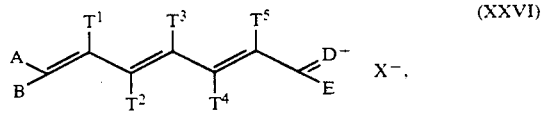

in which $D^+$ represents

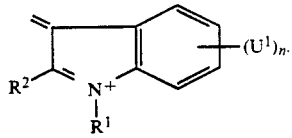

A, B, E, $T^1$ to $T^5$, $R^1$, $R^2$, $U^1$ and n have the abovementioned meaning and $X^-$ represents an anion, and reacting these dyestuffs, preferably without intermediate isolation, with HG (XXI) and a base.

Suitable solvents are alcohols, esters, chlorinated hydrocarbons, ketones, aromatic compounds, chlorinated aromatic compound and nitriles, as are described above under 1.

Suitable acids are inorganic acids, carboxylic acids, sulphonic acids or phosphonic acids, as are described above under 1.

Suitable bases are amines, hydroxides, carbonates or alcoholates, as are described above under 1.

The invention in addition relates to mixtures of the compounds I to IV. The substituents A, B, D, E and $T^1$ to $T^5$ can be identical to or different from one another. The mixtures can be obtained by mixing the components.

Mixtures are preferred which are obtained directly in process 1. Depending on the substituents of the starting components and their mixtures, they may contain a number of isomers.

Such mixtures are as a rule distinguished by particularly good solubility in the solvents customary in use.

The tetraindolylheptamethine derivatives of the formulae I to IV and their mixtures are colourless to brownish coloured solids.

Solutions in acetic acid show a strong absorption having a maximum in the range from 750-950 nm. A very weak absorption having a maximum in the 500-650 nm range is additionally found.

If a toluene solution which is colourless to beige-coloured is brought into contact with acidic clay or silica gel, a bluish to greenish grey coloration develops spontaneously. A very strong absorption can additionally be measured in the near infrared region from 750-950 nm, for example using Dr. Lange colour measurement system Xenocolor LS 100.

If a sample of a derivative of the formulae I to IV is ground with 2,2-bis-(4-hydroxy-phenyl)-propane, a colourless to beige-coloured powder is obtained. If this powder is heated, for example, in a melting point tube, a strong very dark blue colour is developed from about 100° C.

The tetraindolylheptamethine derivatives of the formulae I to IV are therefore excellently suitable according to the invention for pressure-sensitive or heat-sensitive recording materials which can be read in the infrared region from 750-950 nm.

Recording materials which absorb in the near infrared are required in order to be able to read the recorded information using suitable equipment. The spreading of computers and automated data processing necessitate equipment which can read information from documents. Devices for optical character recognition (OCR) were therefore developed which can read pages of text which are typed in the particular typeface programmed in. Customarily, such devices work in the near infrared and therefore the typeface to be read must naturally have absorptions in the near infrared. However, customary pressure-sensitive and heat-sensitive recording materials do not have such an absorption in the near infrared.

Recording materials which have such an absorption in the near infrared are, for example, described in U.S. Patent Specifications 4,020,056, 4,022,771, 4,026,883, 4,107,428 and 4,119,776 and in European Application 0,124,377.

The tetraindolylheptamethine derivatives of the formulae I to IV according to the invention and their mixtures are therefore outstandingly suitable for such OCR-readable recording materials. To this end, in addition to their strong absorption in the region from 750-950 nm, in particular the low absorption in the visible spectral region is particularly advantageous since the compounds according to the invention can therefore be added in a simple manner to existing colour-forming mixtures which develop in a known manner, for example, blue or black colour shades, without this colour shade being noticeably influenced by the developed colour shade of the compounds according to the invention.

Suitable colour formers with which the tetraindolylheptamethine derivativas of the formula I to IV according to the invention can be mixed are derived, for example, from the phthalide, fluorane, spirodipyrane, chromenoindole, phenoxazine, phenothiazine, carbazolylmethane, dihydroquinazolone, dihydro-3,1-benzoxazin-2-one, 3,1-benzoxazine or other triarylmethane leuko dyestuff classes of substances.

The production of such pressure-sensitive or heat-sensitive recording materials is carried out in a known manner.

A pressure-sensitive material consists, for example, of at least one pair of leaves, which contain at least one colour former of the formulae I to IV dissolved or dispersed in a non-volatile organic solvent and an acidic developer.

Such processes and preparations are, for example, disclosed in U.S. Patent Specifications 2,800,457, 2,800,458, 2,948,753, 3,096,189 and 3,193,404 and in German Published Specifications 2,555,080 and 2,700,937.

In order to prevent a premature activation of the colour formers present in the pressure-sensitive recording material, these are preferably sealed into microcapsules which as a rule can be broken by pressure.

Suitable capsule wall materials are, for example, gelatine/gum arabic, polyamides, polyurethanes, polyureas, polysulphonamides, polyesters, polycarbonates, polysulphonates, polyacrylates and phenol-, melamine- or urea-formaldehyde condensates, such as are described, for example, in M. Gutcho, Capsule Technology and Microencapsulation, Noyes Data Corporation 1972, G. Baster, Microencapsulation, Processes and Applications, publisher J. E. Vandegaar and German Published Specifications 2,237,545 and 2,119,933.

Preferably, microcapsules are used whose shells consist of polyaddition products of polyisocyanates and polyamines.

Isocyanates, amines, solvents and a suitable preparation process for such microcapsules are described, for example, in DE-OS (German Published Specification) 3,203,059.

Microcapsules are also preferably used whose shells consist of polyamides or melamine-formaldehyde condensates or gelatine/gum arabic.

Developers which may be mentioned are clays, acid-modified clays, oxides or acid salts and monomeric or polymeric phenols or carboxylic acids.

Particularly preferred colour developers are salts of an aromatic carboxylic acid having at least 10 carbon atoms of the formula

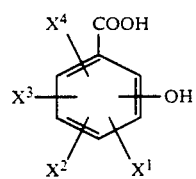

in which $X^1$, $X^2$, $X^3$ and $X^4$ denote hydrogen, halogen, hydroxyl, alkyl, cycloalkyl, aryl, aralkyl, alkoxy or aryloxy, or two adjacent radicals $X^1$, $X^2$, $X^3$ and $X^4$ can together form a ring, and where these radicals may carry the abovementioned non-ionic substituents customary in dyestuff chemistry. Compounds of this type are described, for example, in DE-OS (German Published Specification) 3,635,311 and 3,635,742.

The tetraindolylheptamethine derivatives of the formula I to IV are as a rule sufficiently to very readily soluble in the non-volatile organic solvents customary for microencapsulation.

Heat-reactive recording systems include, for example, heat-sensitive recording and copying materials and papers.

Such a material is described, for example, in DE-OS (German Published Specification) 2,555,080.

Suitable developers are the same electron acceptors as are used in pressure-sensitive papers, preferably phenolic compounds, which are described, for example, in German Patent Specification 1,251,348, and also boric acid and organic, preferably aliphatic, dicarboxylic acids.

Another suitable heat-reactive developer system is described in DE-OS (German Published Specification) 3,337,296, in which acid-modified polymers, preferably of acrylonitrile, act as developers.

EXAMPLE 1

29.5 g of 1;1-bis-(1-benzyl-2-phenyl-indol-3-vl-)-ethene and 4.3 g of 1,1,3,3-tetramethoxypropane are stirred for 1 h at 80° C. in a mixture of 50 ml of acetic anhydride and 2.5 g of methanesulphonic acid. The very dark blue solution is discharged into 200 ml of methanol and 8.9 g of p-toluenesulphinic acid sodium salt are added. After addition of 60 g of anhydrous sodium carbonate, the greenish beige product is filtered off with suction, washed with methanol and water and dried: 33.4 g (97.4% of theory) of greenish beige powder of melting point 174° C.

In an isomeric form, the product corresponds to the formula:

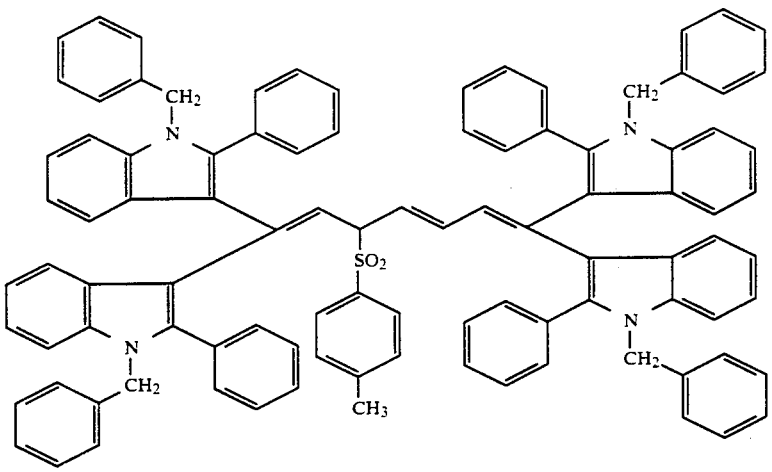

A solution in glacial acetic acid shows a dirty blue colour and $\lambda_{max}=875$ nm. A solution in toluene develops a pale grey-green colour on acid clay. An absorption from 750–950 nm can be measured in the infrared.

EXAMPLE 2

25 g of the ether of the formula

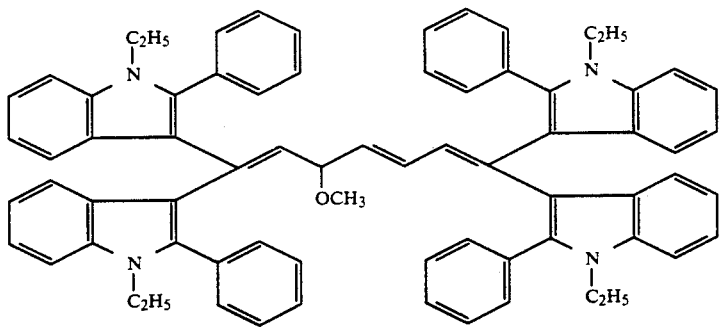

are dissolved with 3.5 g of methanesulphonic acid in 100 ml of acetonitrile 7 5 g of phthalimide and 30 g of anhydrous sodium carbonate are added. The mixture is stirred at 40° C. for 10 min. After cooling, it is filtered with suction. The product is stirred in 100 ml of methanol, filtered off with suction and washed with methanol and water. After drying, 20.1 g (71.7%) of brownish beige powder of melting point 160°–164° C. are obtained In an isomeric form, this corresponds to the formula:

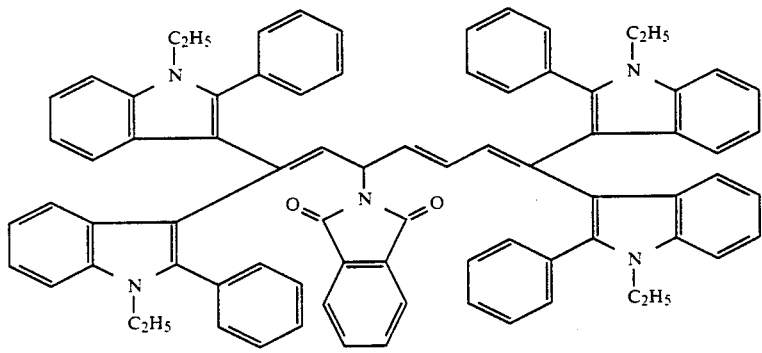

IR: 1,706 cm$^{-1}$.
$\lambda_{max}$ in glacial acetic acid: 864 nm.
On acid clay: greenish grey, 750–950 nm.

The ether employed as starting material is prepared as follows: 23.3 g of 1,1-bis-(1-ethyl-2-phenyl-indol-3-yl)-ethene and 4.3 g of 1,1,3,3-tetramethoxypropane are stirred for 1 h at 90° C. in a mixture of 50 ml of acetic anhydride and 2.5 g of methanesulphonic acid. The very dark blue solution, which contains the dyestuff of the formula

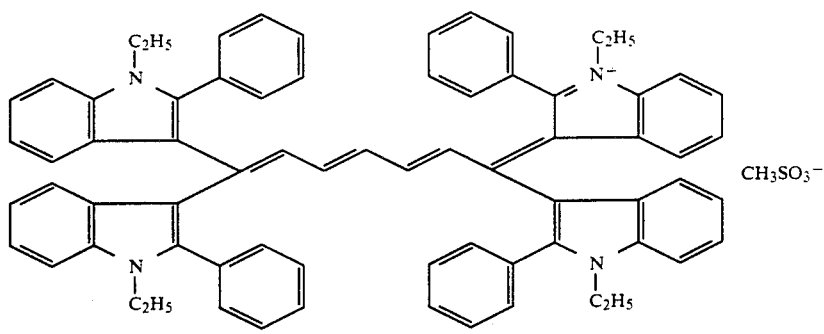

is discharged into 200 ml of methanol, rendered alkaline using 70 ml of 30% strength methanolic sodium methoxide solution and boiled for 2 h. The beige-brown product is filtered off with suction after cooling, washed with methanol and water and dried: 20.9 g(83.6% of theory) of brownish beige powder of melting point 176°–178° C.

EXAMPLE 3

25 g of the ether of the formula

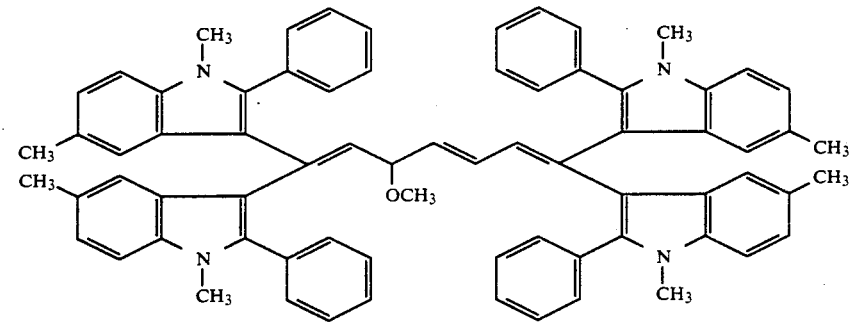

are reacted with 3.4 g of methanesulphonic acid in 100 ml of acetonitrile to give a blue dyestuff solution 3.5 g of 1,2,4-triazole and 20 g of anhydrous sodium carbonate are added and the mixture is stirred at 30°–40° C. for ½ h. The brownish beige suspension is stirred until cold, filtered off with suction and washed with methanol and water. 19.5 g (75%) of pale beige powder of melting point 227°–229° C. are obtained. In an isomeric form, this corresponds to the formula:

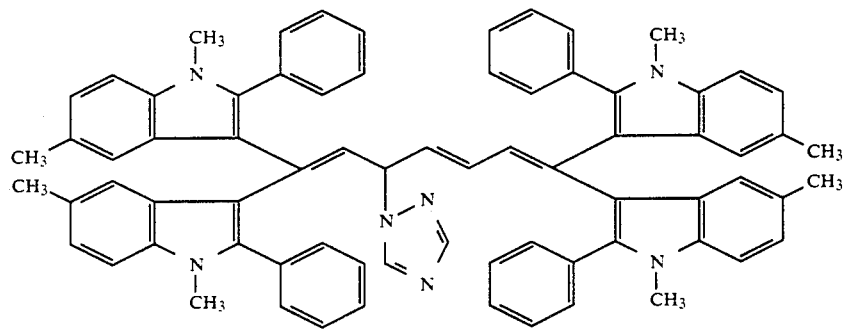

$\lambda_{max}$ in glacial acetic acid: 863 nm.
On acid clay: green-blue, 750–950 nm.
The preparation of the ethers employed here and in the following examples is carried out analogously to the process indicated in Example 2.

EXAMPLE 4

24.3 g of the ether of the formula

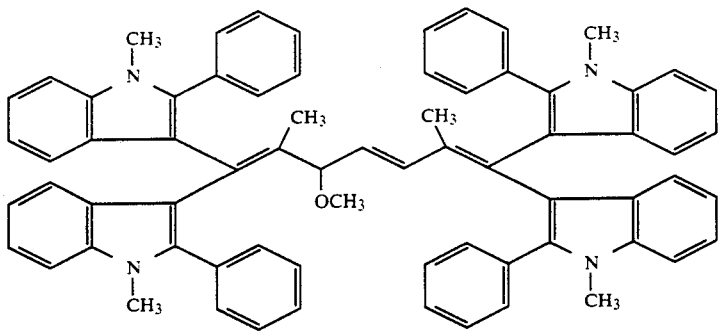

are stirred with 2.65 g of methanesulphonic acid in 130 ml of methanol for 30 min at 50° C. 2.7 g of malodinitrile and 8 g of anhydrous sodium carbonate are then added. The mixture is stirred at 50° C. for 7 h. After cooling, it is filtered with suction and the precipitate is washed with methanol and water. The product is dried and then boiled in 100 ml of ethanol. After cooling, the precipitate is filtered off with suction, washed with ethanol and water and dried. 20.0 g (79.4% of theory) of brownish beige powder of melting point 194°-200° C. are thus obtained. In an isomeric form, this corresponds to the formula:

$\lambda_{max}$ in glacial acetic acid: 866 nm.
On acid clay: grey, 750-950 nm.

EXAMPLE 5

5 g of the ether of the formula

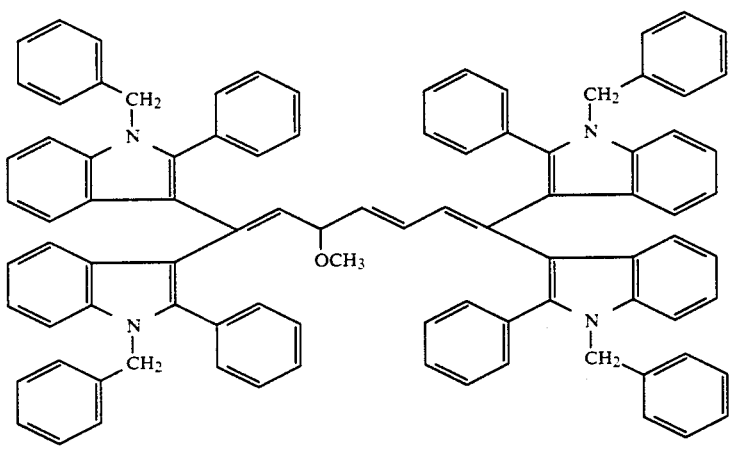

are dissolved in 50 ml of methanol with the addition of 1.5 ml of glacial acetic acid. 3 g of acetylacetone are added. A pale blue suspension is immediately formed which is decolorized with sodium carbonate. The precipitate is filtered off with suction and washed with methanol and water. 5.3 g (99% of theory) of beige powder of melting point 152°-155° C. are thus obtained.

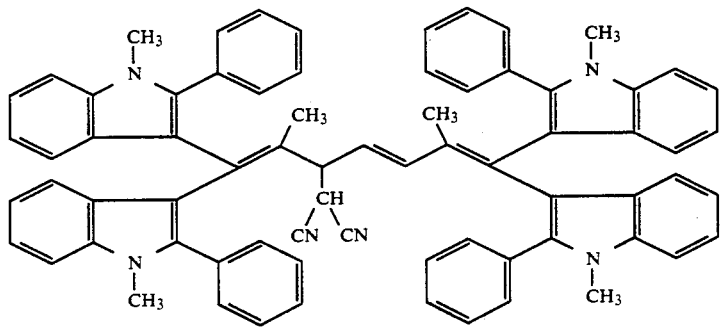

IR: 2,250 cm$^{-1}$.

In an isomeric form, this corresponds to the formula:

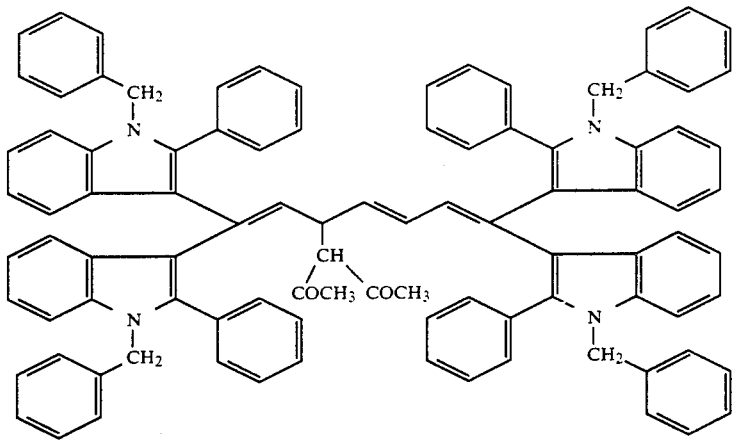

IR: 1,690 cm$^{-1}$.
$\lambda_{max}$ in glacial acetic acid: 875 nm.
On acid clay: greenish grey, 750–950 nm.

EXAMPLE 6

5.4 g of the ether of the formula

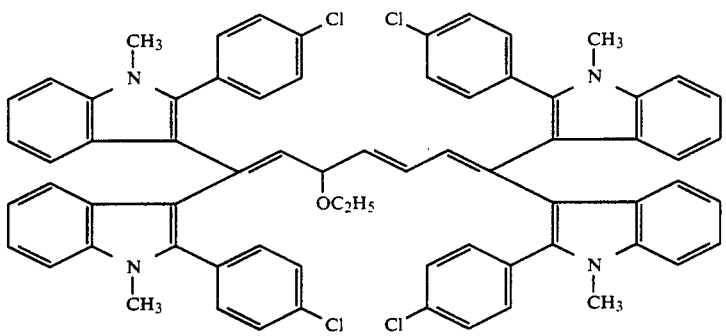

are dissolved with a blue colour in the presence of heat in 20 ml of acetonitrile with the addition of 2 g of glacial acetic acid. 2.8 g of aniline and 8 g of anhydrous sodium carbonate are added and the mixture is stirred at 40° C. for 3 h. A precipitate gradually deposits. The suspension is stirred until cold, filtered with suction and the precipitate is washed with acetonitrile and water. After drying, 4.4 g (96% of theory) of beige powder of melting point 170°–172° C. are obtained. In an isomeric form, this corresponds to the formula:

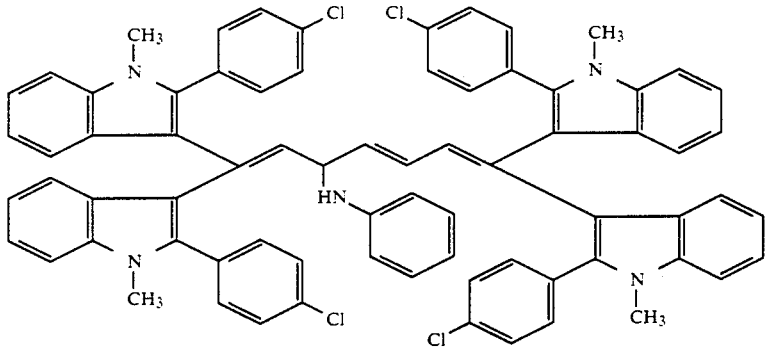

$\lambda_{max}$ in glacial acetic acid: 866 run.

On acid clay: grey-green, 750–950 nm.

EXAMPLE 7

5 g of the ether of the formula

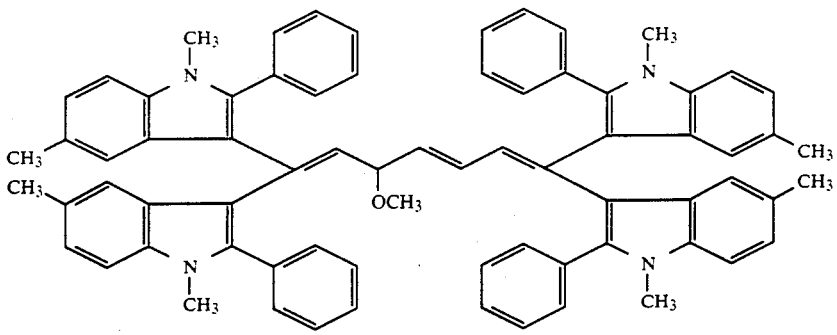

are dissolved in 30 ml of methanol with 0.7 g of methanesulphonic acid. 1.3 g of 3-methyl-1-phenyl-2-pyrazolin-5-one and 10 g of anhydrous sodium carbonate are added at room temperature. After stirring for 1 h with gentle cooling, the mixture is filtered with suction, and the precipitate is washed with methanol and water and dried in a desiccator: 4.3 g (75.2% of theory) of beige powder of melting point 160°–615° C.

In an isomeric form, this corresponds to the formula:

$\lambda_{max}$ in glacial acetic acid: 863 nm.
On acid clay: bluish grey, 750–950 nm.

EXAMPLE 8

5.4 g of the ether of the formula

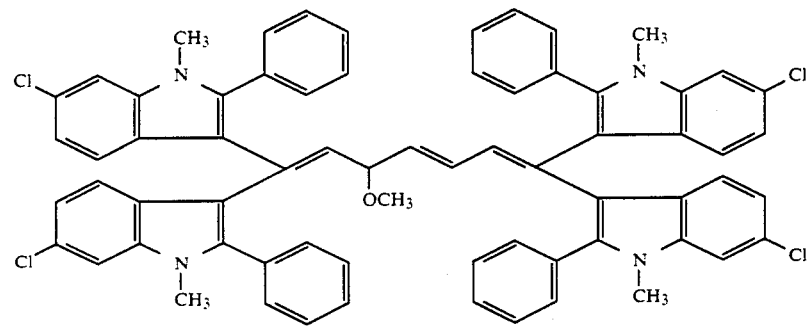

are stirred for 4 h in 20 ml of acetonitrile with 0.73 g of Meldrum's acid. The mixture is discharged into 200 ml of water, filtered with suction, and the precipitate is washed with water and dried: 4.5 g (75.4% of theory) of brown powder of melting point 200°–205° C. (dec.). In an isomeric form, this corresponds to the formula:

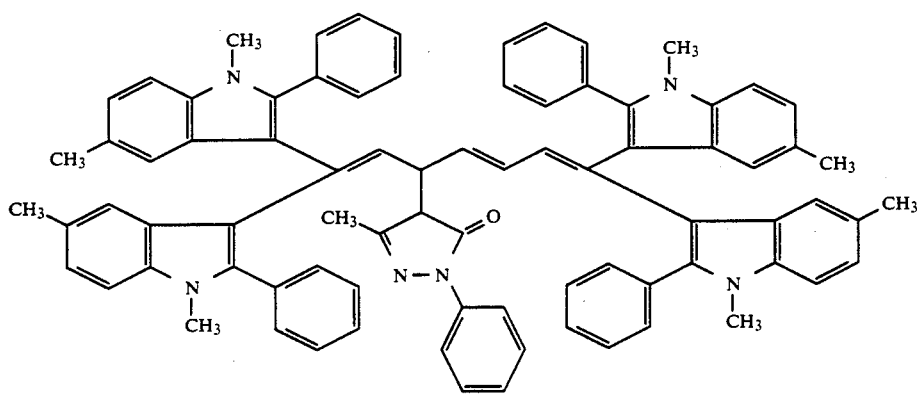

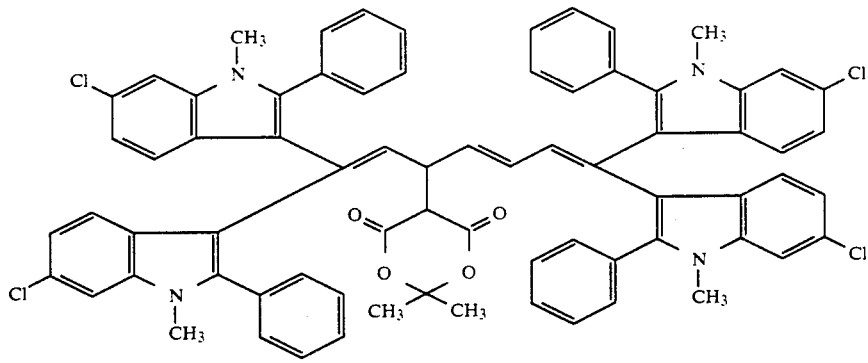

IR: 3,420, 1,741 cm$^{-1}$.
$\lambda_{max}$ in glacial acetic acid: 865 nm.
On acid clay: greenish grey, 750–950 nm.

filtered with suction, and the precipitate is washed with methanol and water and dried: 4.5 g (78% of theory) of brown-beige powder of melting point 178°–180° C. In an isomeric form, this has the formula:

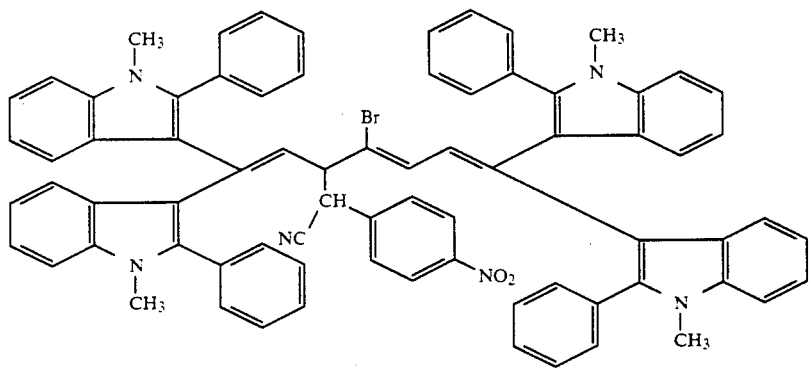

EXAMPLE 9

5.12 g of the ether of the formula

IR: 2,235, 1,520, 1,340 cm$^{-1}$.
$\lambda_{max}$ in glacial acetic acid: 869 nm.

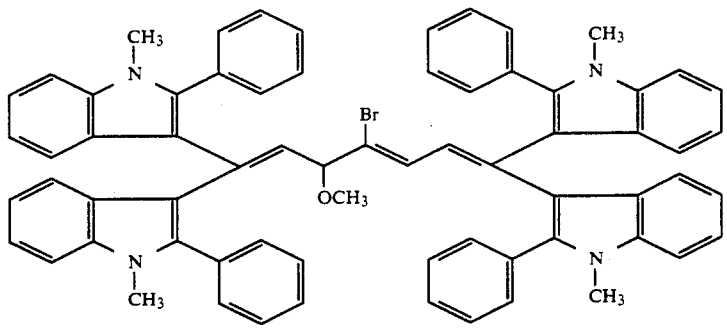

are dissolved in 20 ml of acetonitrile at 40 C. with the addition of 0.67 g of methanesulphonic acid. 1.62 g of 4-nitrobenzyl cyanide and 3.5 g of anhydrous sodium carbonate are added. After 20 min at 40° C., the mixture is cooled. 50 ml of methanol are added. The mixture is On acid clay: grey-green, 750–950 nm.

EXAMPLE 10

41 g of the ether of the formula

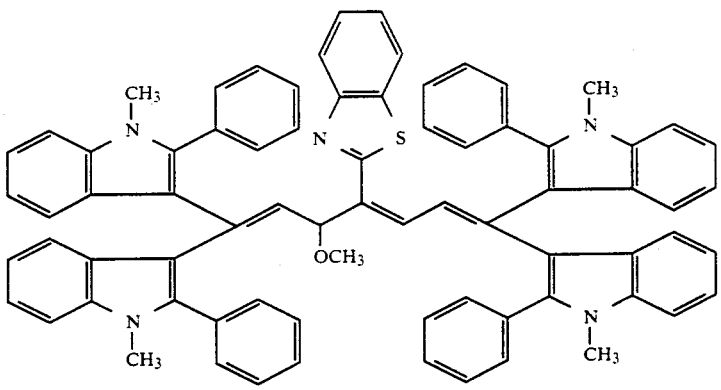

are dissolved in 150 ml of acetonitrile with 5 g of methanesulphonic acid. 21 g of pyrrolidine are added thereto. A yellow suspension results which is filtered with suction, and the precipitate is washed with acetonitrile and dried: 34 g (74.3% of theory) of yellow powder of melting point 233°–235° C. In an isomeric form, this has the formula:

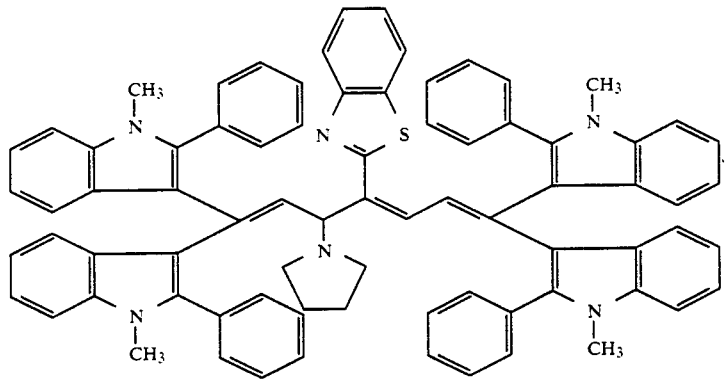

$\lambda_{max}$ in glacial acetic acid: 859 nm.
On acid clay: greenish grey, 750–950 nm.
The following examples can be prepared analogously to Examples 1–10:

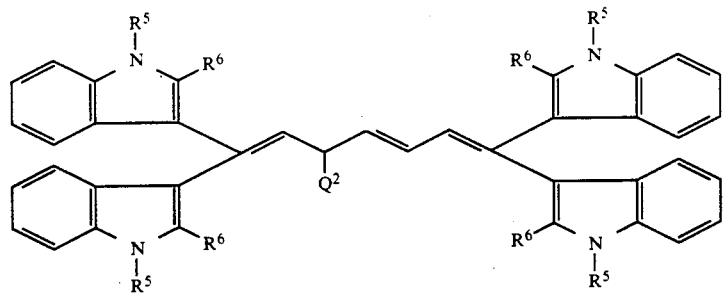

| Example | R⁵ | R⁶ | Q² | $\lambda_{max}$ in glacial acetic acid |
|---|---|---|---|---|
| 11 | —CH₃ | —C₆H₅ | —SO₂C₈H₁₇ | 863 nm |
| 12 | n-C₄H₉ | —C₆H₅ | —CH(COOC₂H₅)(CN) | 867 nm |

-continued
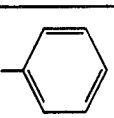
| Example | R⁵ | R⁶ | Q² | λ$_{max}$ in glacial acetic acid |
|---|---|---|---|---|
| 13 | n-C₈H₁₇ | 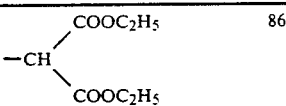 | 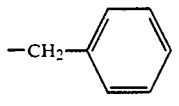 | 867 nm |
| 14 | 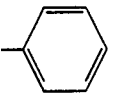 | 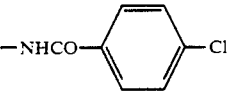 |  | 874 nm |
| 15 | —CH₃ | 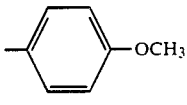 | 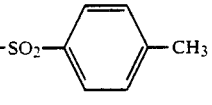 | 870 nm |
| 16 | —CH₃ |  | 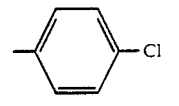 | 865 nm |
| 17 | —CH₃ | 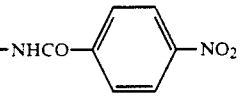 |  | 862 nm |
| 18 | —CH₃ | 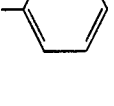 | 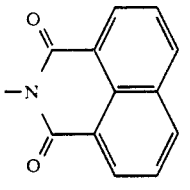 | 859 nm |
| 19 | —CH(CH₃)₂ |  | 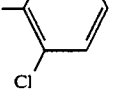 | 867 nm |
| 20 | —CH₃ | 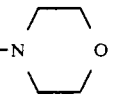 |  | 863 nm |
| 21 | —CH₃ | —CH₃ | 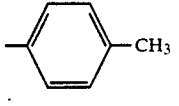 | 818 nm |
| 22 | 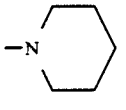 | —CH₃ |  | 824 nm |

-continued
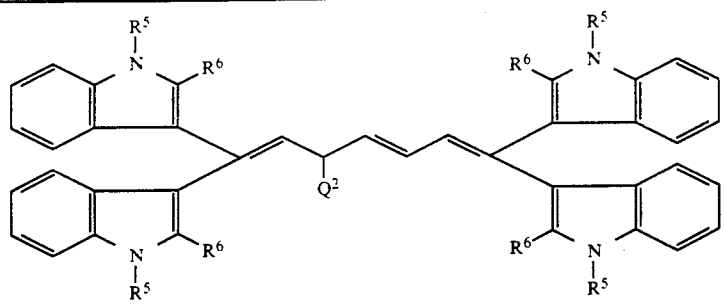
| Example | $R^5$ | $R^6$ | $Q^2$ | $\lambda_{max}$ in glacial acetic acid |
|---|---|---|---|---|
| 23 | —CH₃ | n-C₄H₉ | (barbituric acid-type group) | 820 nm |
| 24 | —CH₃ | n-C₈H₁₇ | (dibenzoylmethyl group) | 820 nm |
| 25 | —CH₂CH₂CN | phenyl | —NHSO₂CH₃ | 852 nm |
| 26 | —C₂H₄OCH₃ | n-C₆H₁₃ | —S—phenyl | 825 nm |
EXAMPLE 27
$\lambda_{max}$ in glacial acetic acid: 857 nm.
EXAMPLE 28
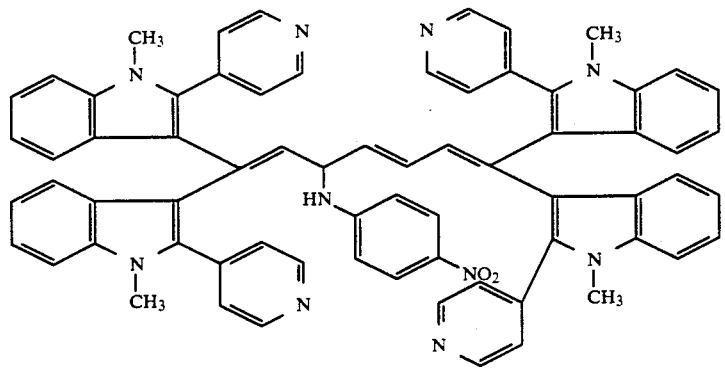

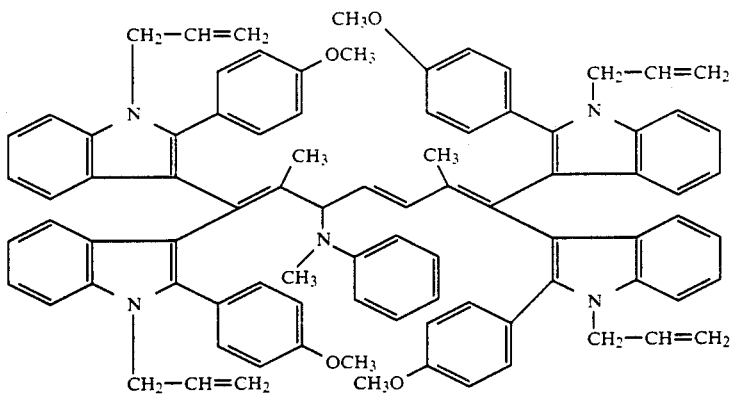
λ$_{max}$ in glacial acetic acid: 872 nm.
EXAMPLE 29
λ$_{max}$ in glacial acetic acid: 870 nm.
EXAMPLE 31
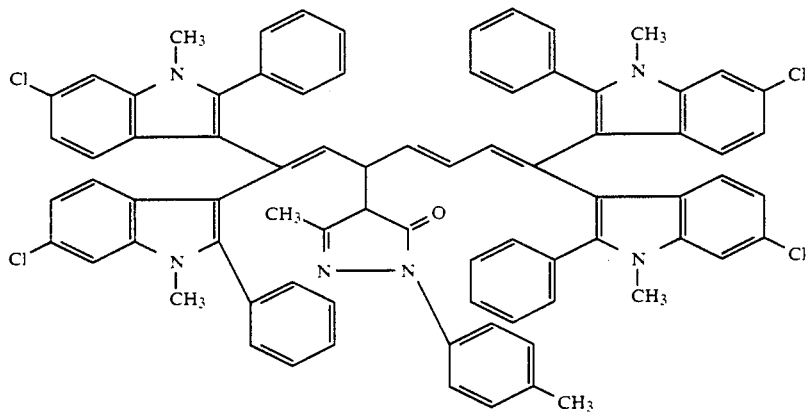
λ$_{max}$ in glacial acetic acid: 865 nm.
EXAMPLE 30
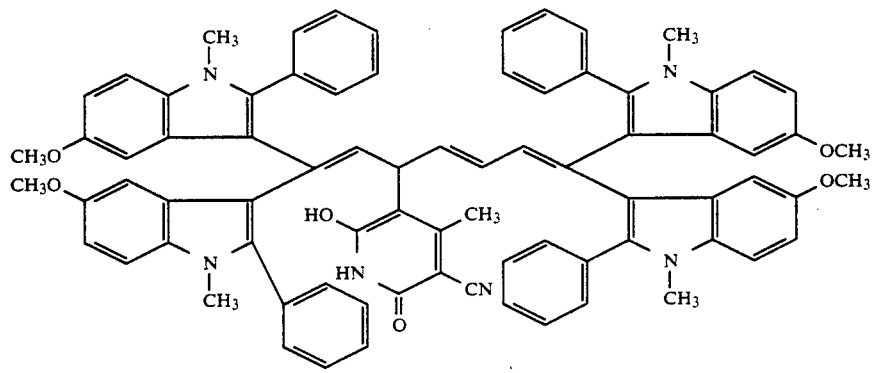

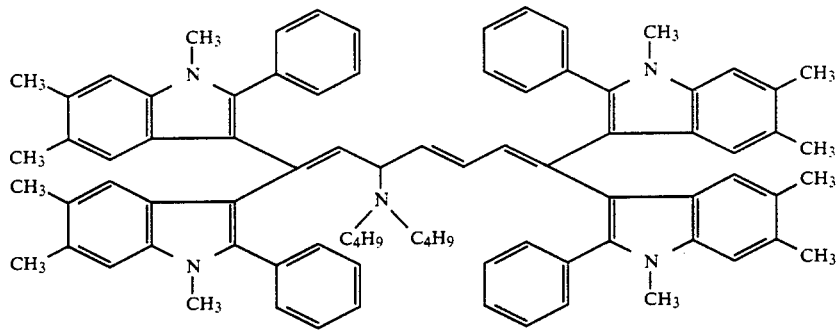
λ$_{max}$ in glacial acetic acid: 865 nm.
EXAMPLE 32
λ$_{max}$ in glacial acetic acid: 862 nm.
EXAMPLE 34
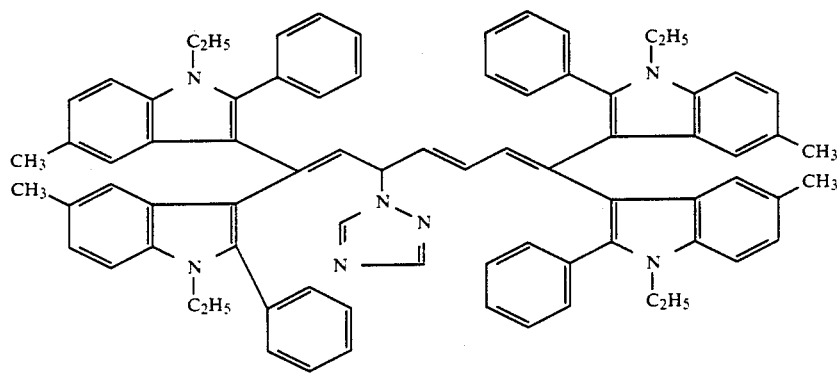
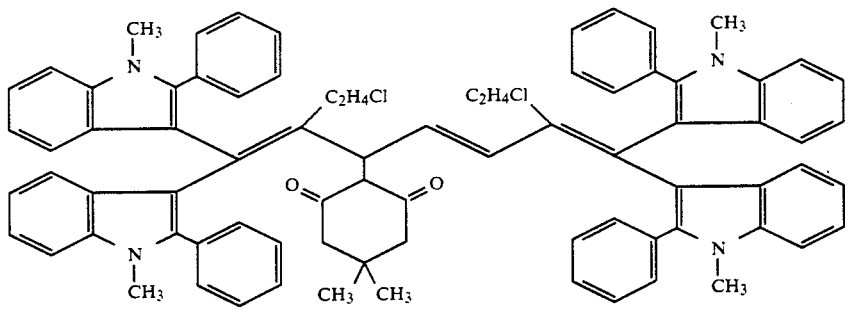
λ$_{max}$ in glacial acetic acid: 864 nm.
EXAMPLE 33
λ$_{max}$ in glacial acetic acid: 867 nm.
EXAMPLE 35
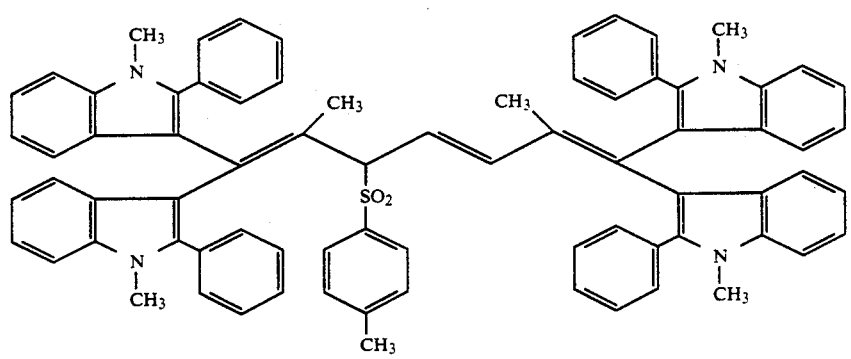

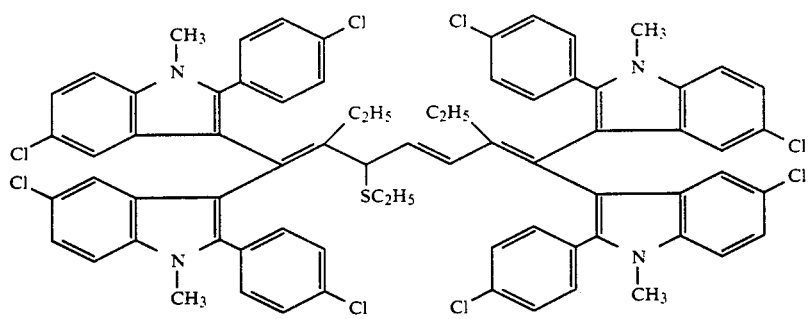
λ$_{max}$ in glacial acetic acid: 863 nm.
EXAMPLE 36
λ$_{max}$ in glacial acetic acid: 791 nm.
EXAMPLE 38
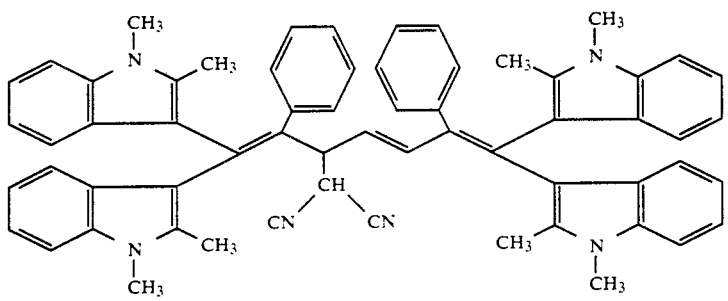
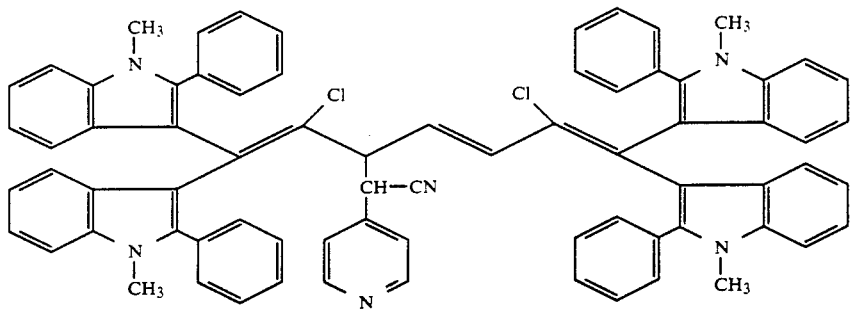
λ$_{max}$ in glacial acetic acid: 800 nm.
EXAMPLE 37
λ$_{max}$ in glacial acetic acid: 900 nm.
EXAMPLE 39
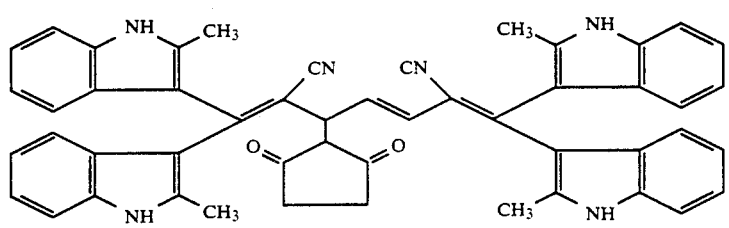

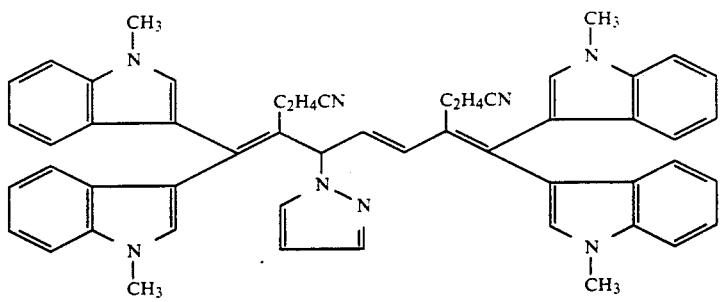
15
λ$_{max}$ in glacial acetic acid: 815 nm.
EXAMPLE 40
λ$_{max}$ in glacial acetic acid: 858 nm.
EXAMPLE 42
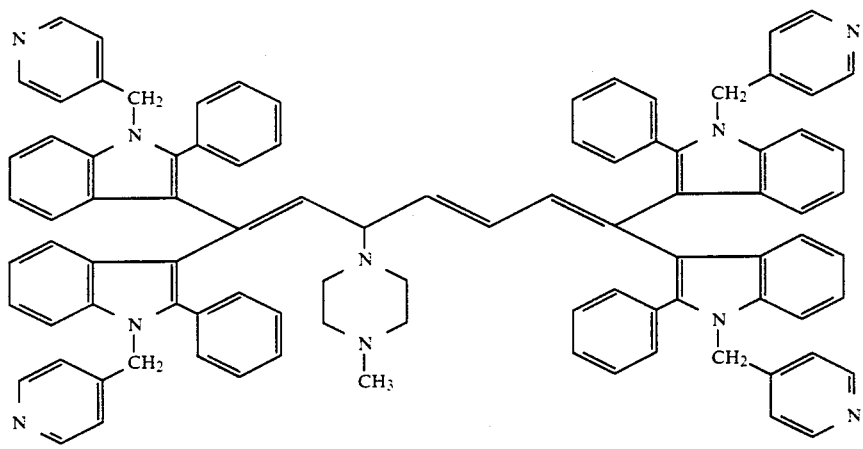
45
λ$_{max}$ in glacial acetic acid: 870 nm.
EXAMPLE 41
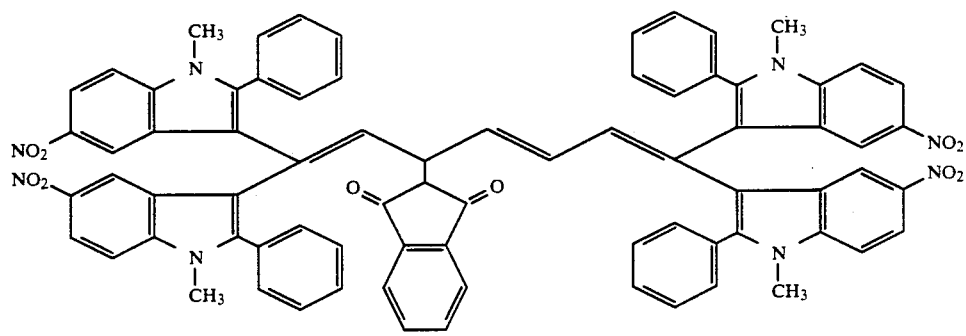

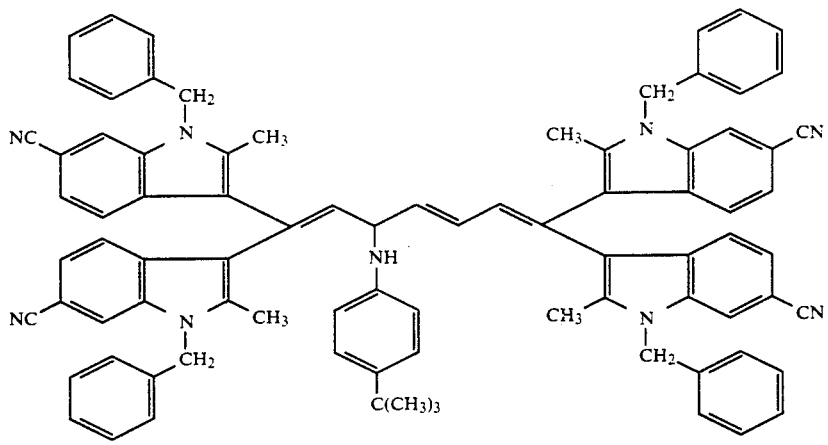
λ$_{max}$ in glacial acetic acid: 830 nm.
EXAMPLE 43
λ$_{max}$ in glacial acetic acid: 895 nm.
EXAMPLE 45
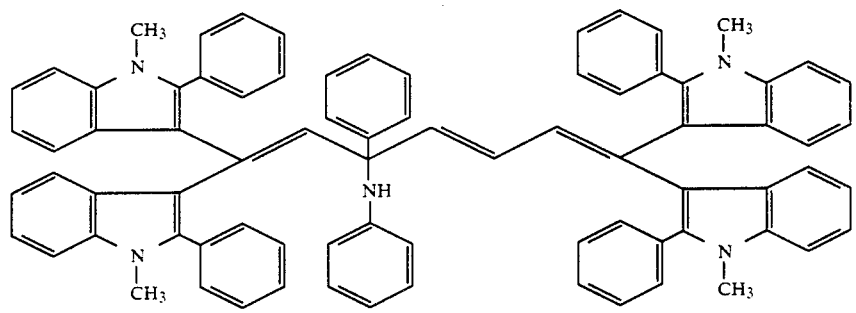
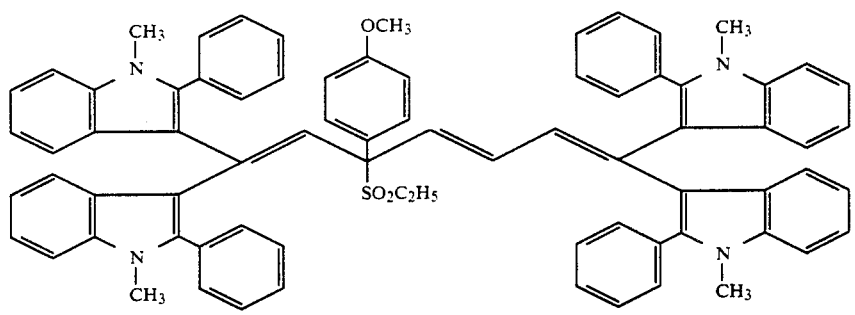
λ$_{max}$ in glacial acetic acid: 897 nm.
EXAMPLE 44
λ$_{max}$ in glacial acetic acid: 885 nm.
EXAMPLE 46
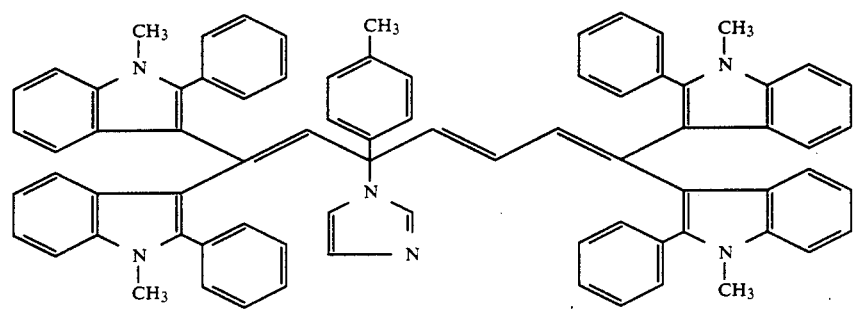

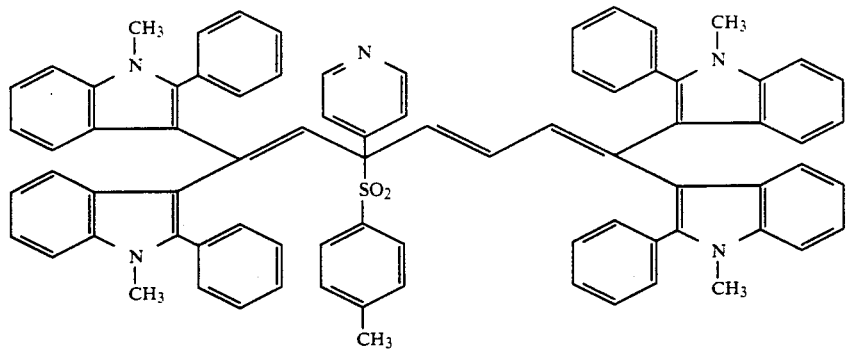
$\lambda_{max}$ in glacial acetic acid: 905 nm.
EXAMPLE 47
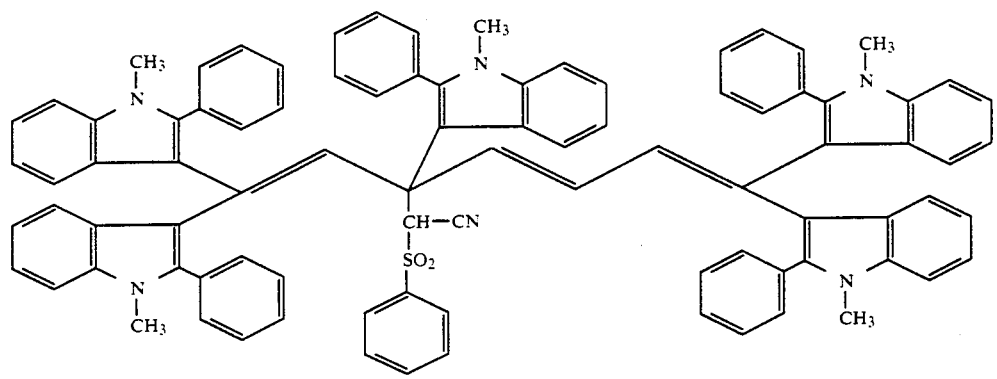
$\lambda_{max}$ in glacial acetic acid: 876 nm.
EXAMPLE 48
$\lambda_{max}$ in glacial acetic acid: 900 nm.
EXAMPLE 49
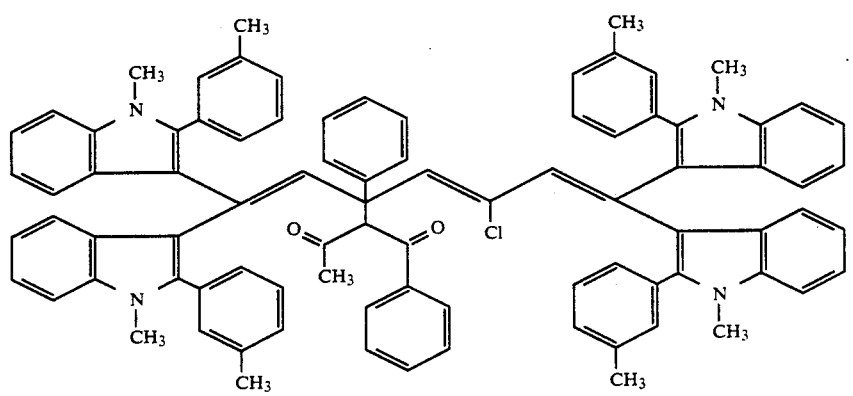

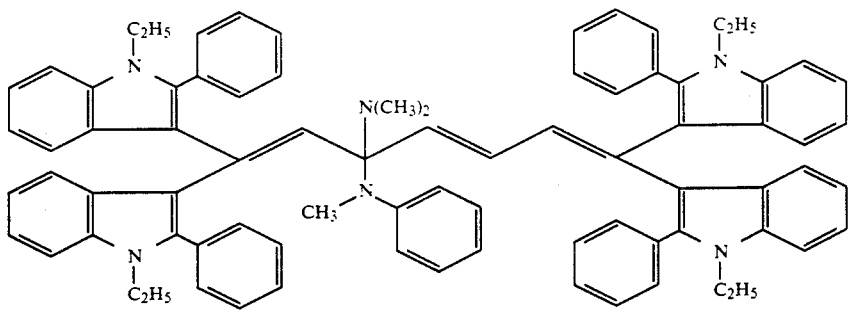
λ<sub>max</sub> in glacial acetic acid: 770 nm.
EXAMPLE 50
λ<sub>max</sub> in glacial acetic acid: 765 nm.
EXAMPLE 52
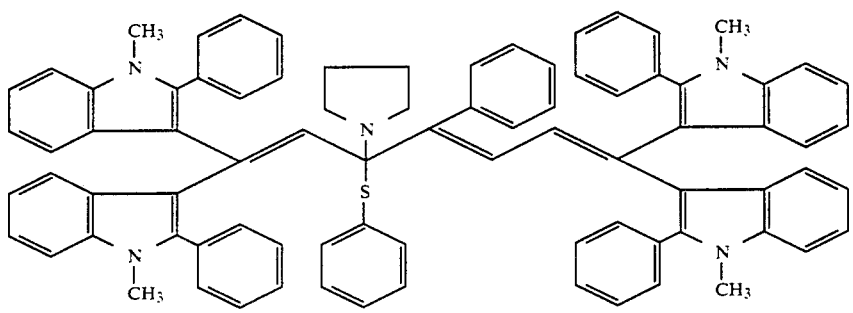
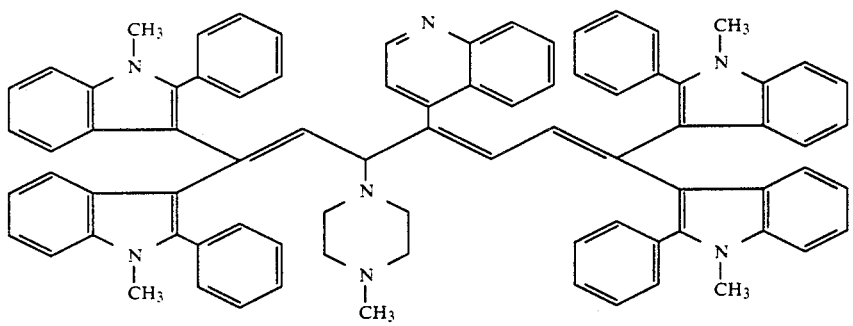
λ$_{max}$ in glacial acetic acid: 802 nm.
EXAMPLE 51
λ$_{max}$ in glacial acetic acid: 856 nm.
EXAMPLE 53
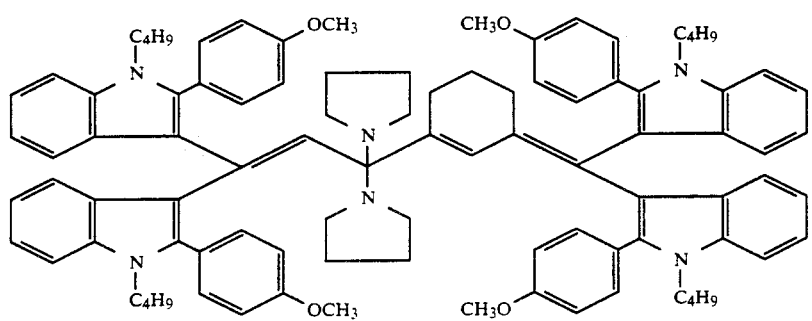

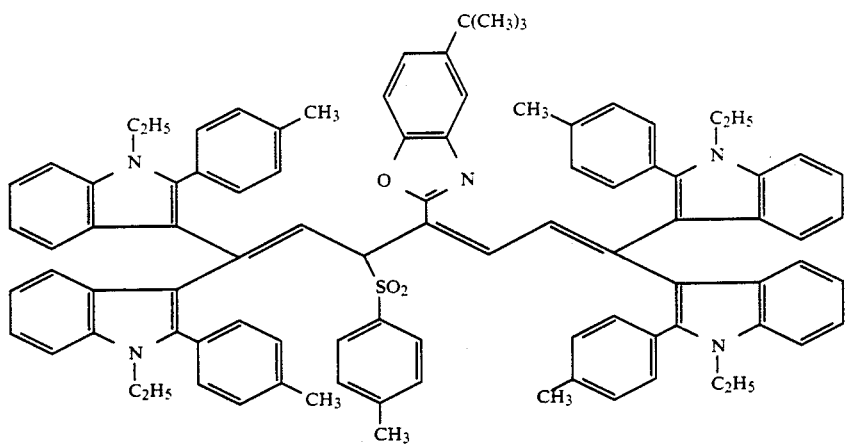
λ<sub>max</sub> in glacial acetic acid: 860 nm.
EXAMPLE 54
λ<sub>max</sub> in glacial acetic acid: 850 nm.
EXAMPLE 56
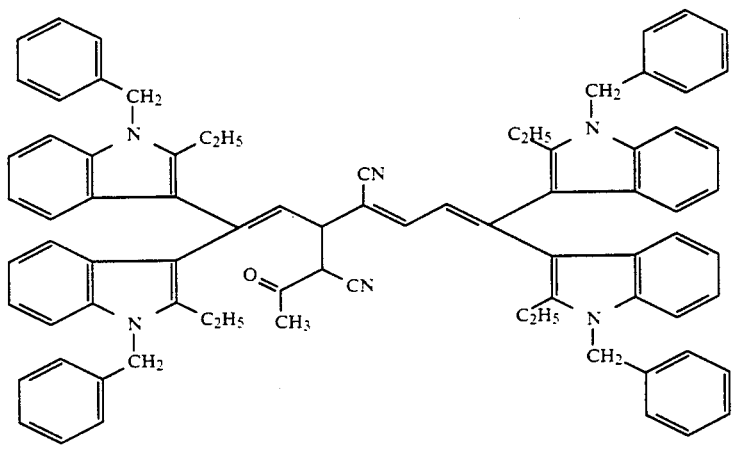
λ<sub>max</sub> in glacial acetic acid: 800 nm.
EXAMPLE 55
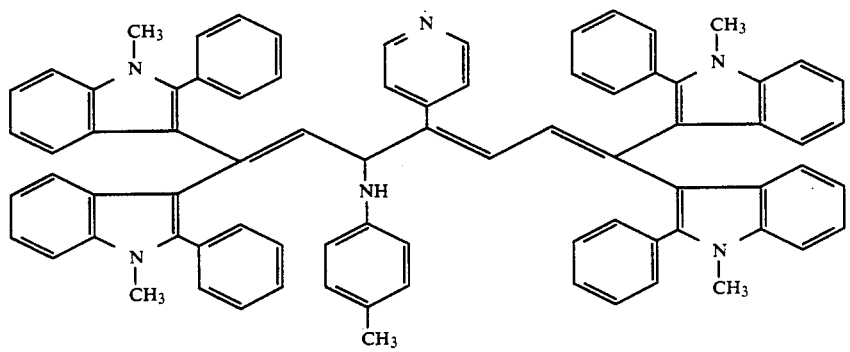

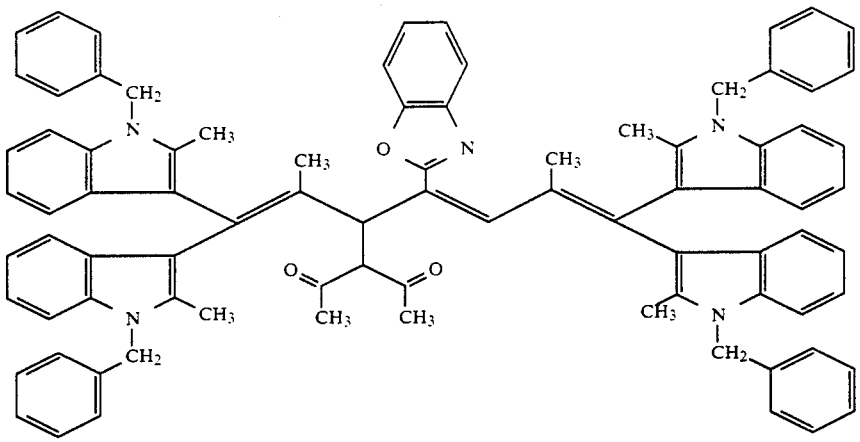
λ$_{max}$ in glacial acetic acid: 815 nm.
EXAMPLE 57
λ$_{max}$ in glacial acetic acid: 800 nm.
EXAMPLE 59
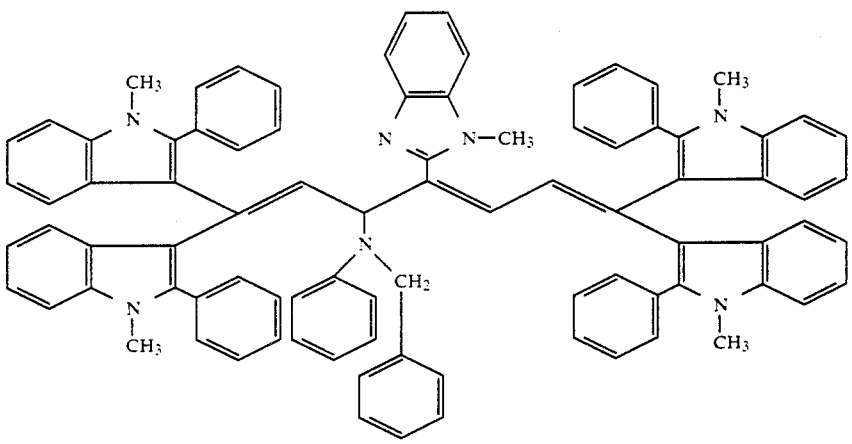
λ$_{max}$ in glacial acetic acid: 858 nm.
EXAMPLE 58
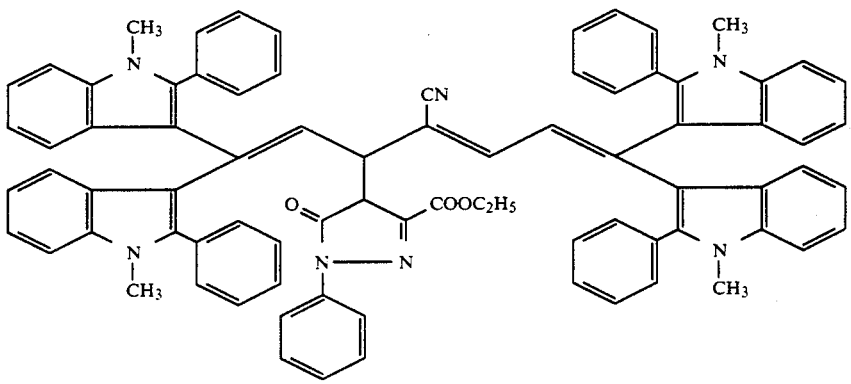

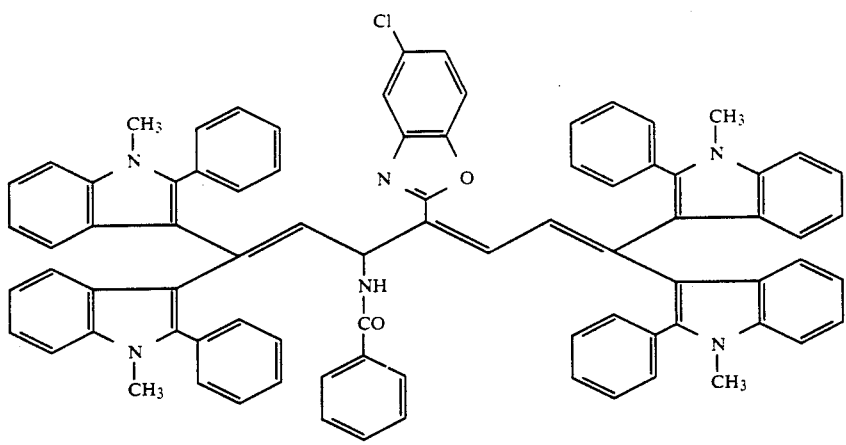
λ$_{max}$ in glacial acetic acid: 859 nm.
EXAMPLE 60
λ$_{max}$ in glacial acetic acid: 859 nm.
EXAMPLE 62
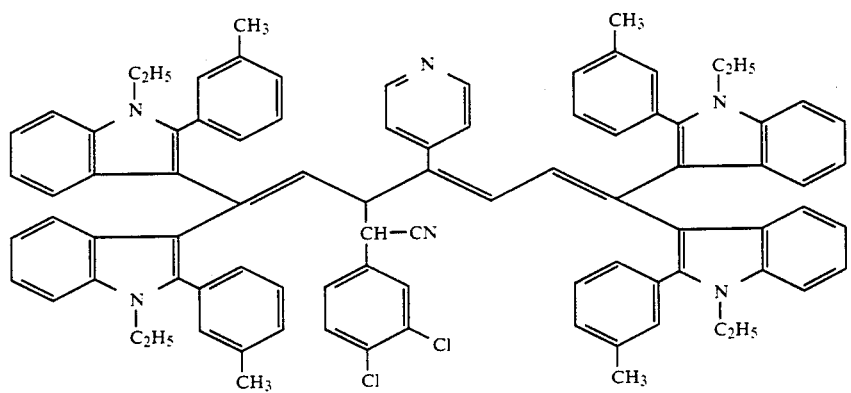
λ$_{max}$ in glacial acetic acid: 851 nm.
EXAMPLE 61
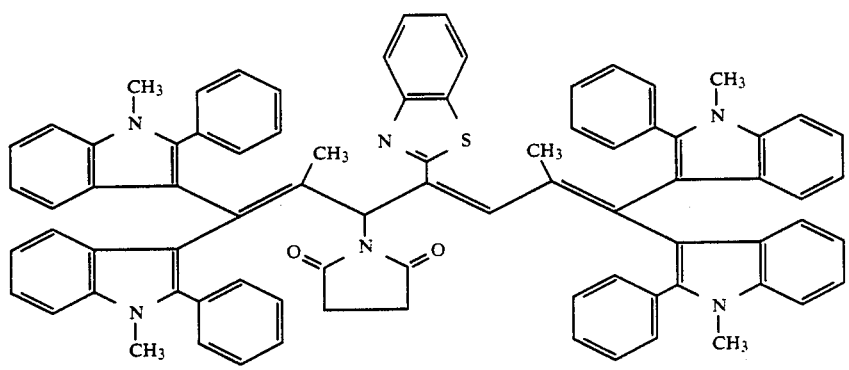

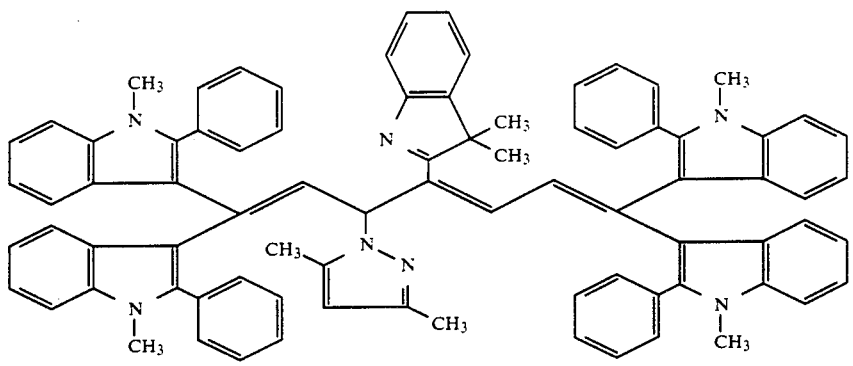
λ$_{max}$ in glacial acetic acid: 857 nm.
EXAMPLE 63
λ$_{max}$ in glacial acetic acid: 859
EXAMPLE 65
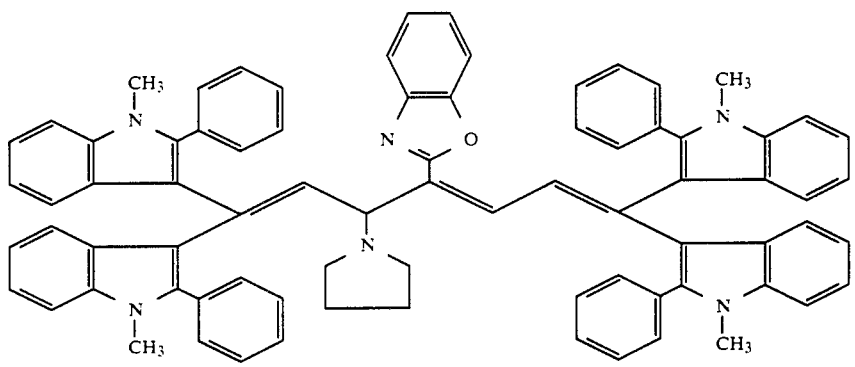
λ$_{max}$ in glacial acetic acid: 858
EXAMPLE 64
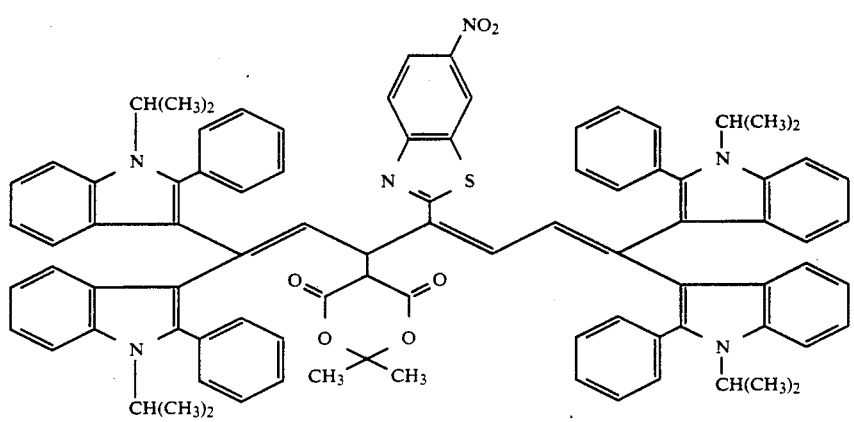

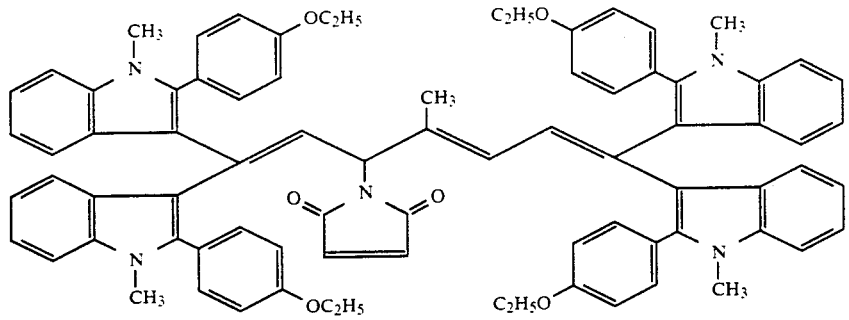
λ<sub>max</sub> in glacial acetic acid: 857 nm.
EXAMPLE 66
λ<sub>max</sub> in glacial acetic acid: 874 nm.
EXAMPLE 68
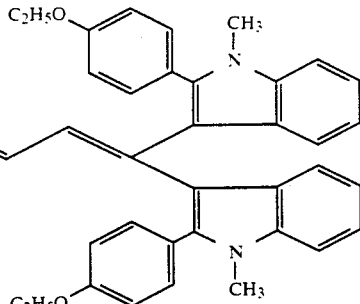
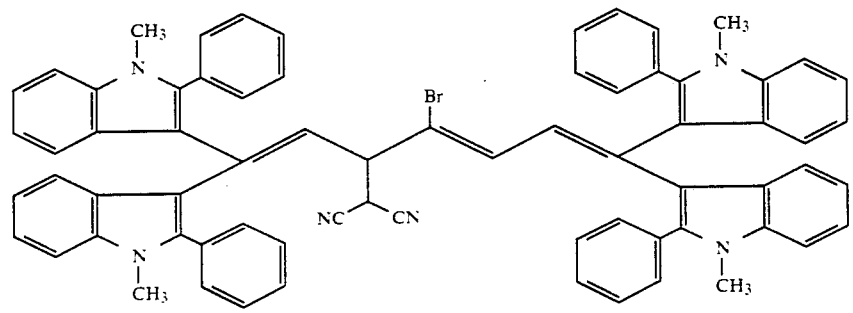
λ<sub>max</sub> in glacial acetic acid: 869 nm.
EXAMPLE 67
λ<sub>max</sub> in glacial acetic acid: 797 nm.
EXAMPLE 69
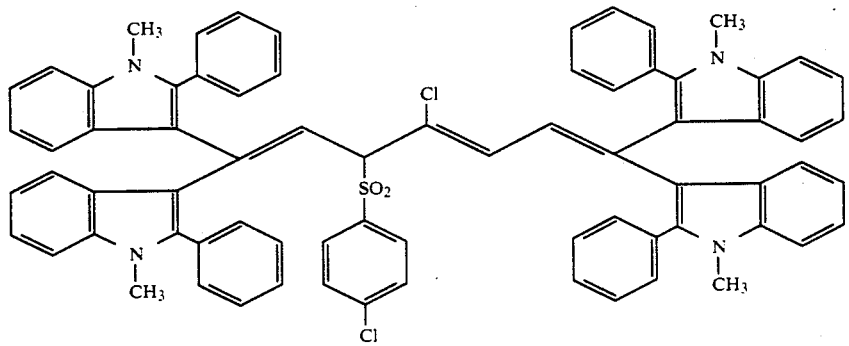

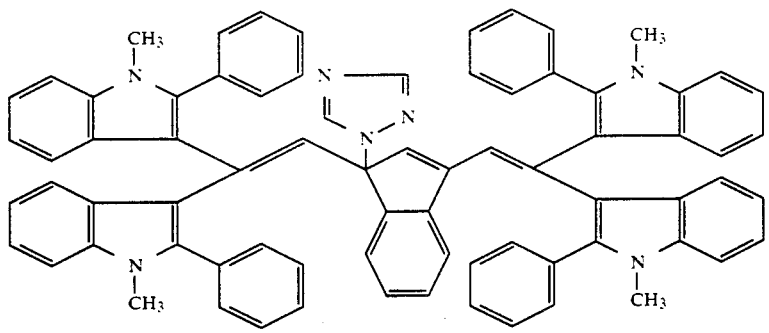
λ_max in glacial acetic acid: 794 nm.
EXAMPLE 70
λ_max in glacial acetic acid: 795 nm.
EXAMPLE 72
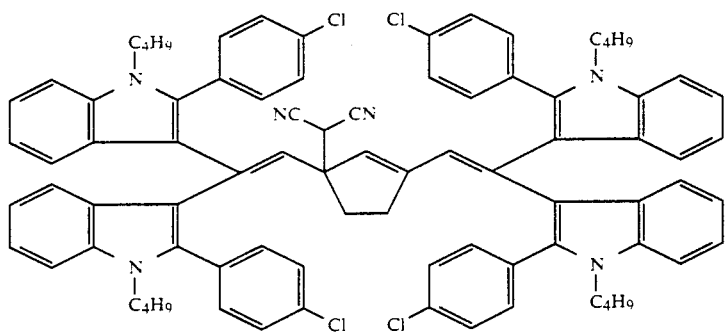
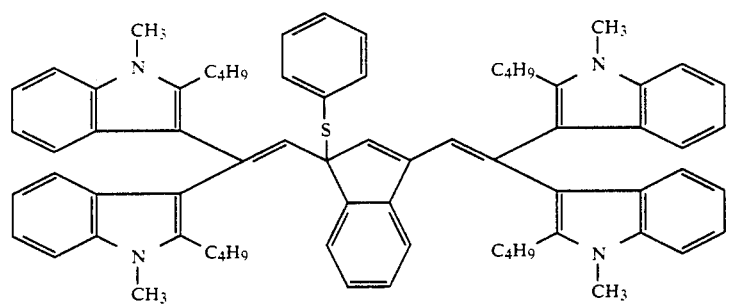
λ_max in glacial acetic acid: 803 nm.
EXAMPLE 71
λ_max in glacial acetic acid: 760 nm.
EXAMPLE 73
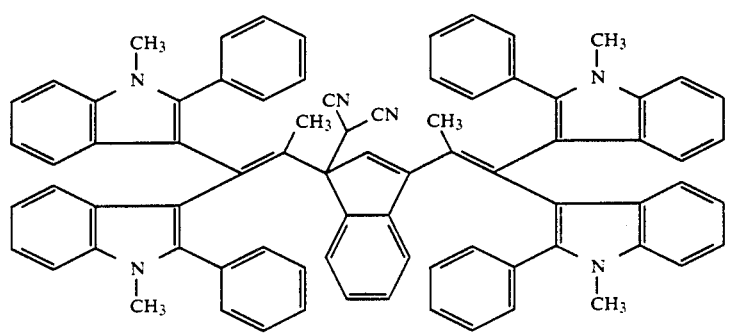

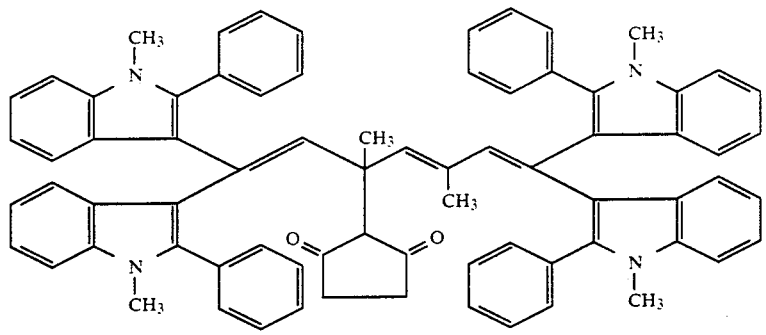

λ$_{max}$ in glacial acetic acid: 798 nm.

EXAMPLE 74

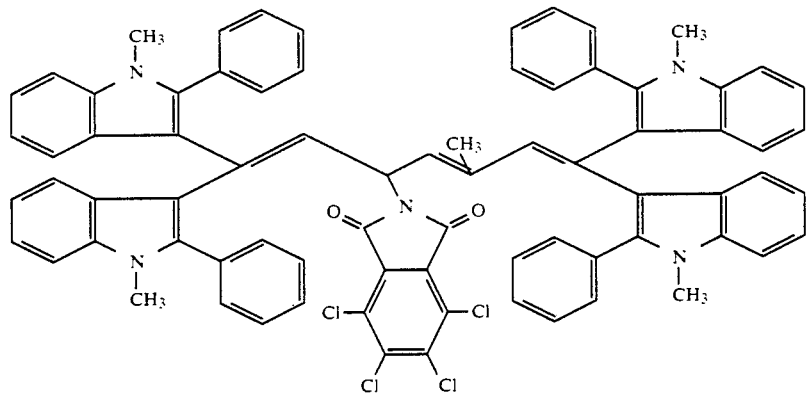

λ$_{max}$ in glacial acetic acid: 880 nm.

EXAMPLE 75

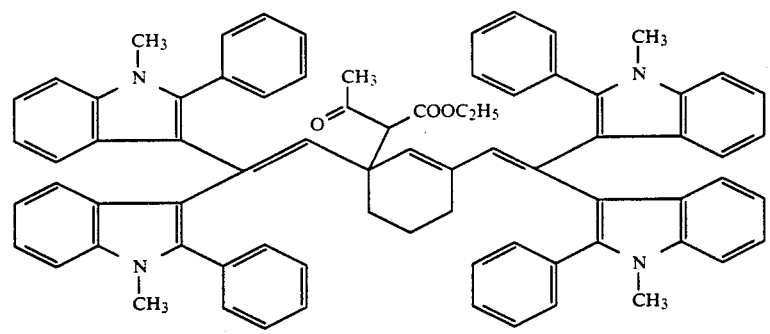

λ$_{max}$ in glacial acetic acid: 796 nm.

EXAMPLE 76

11.3 g of 1,1-bis-(1-methyl-2-phenyl-indol-3-yl-)-propene, 12.5 g of 1,1-bis-(1-methyl-2-(4-methoxy-phenyl)-indol-3-yl)-ethene and 4.3 g of 1,1,3,3-tetramethoxypropane are reacted as in Example 1. 26.2 g of brownish beige powder are obtained, which consists of a mixture (about 3:3:1) of the products of Examples 15, 33 and the compound of the formula (in an isomeric form)

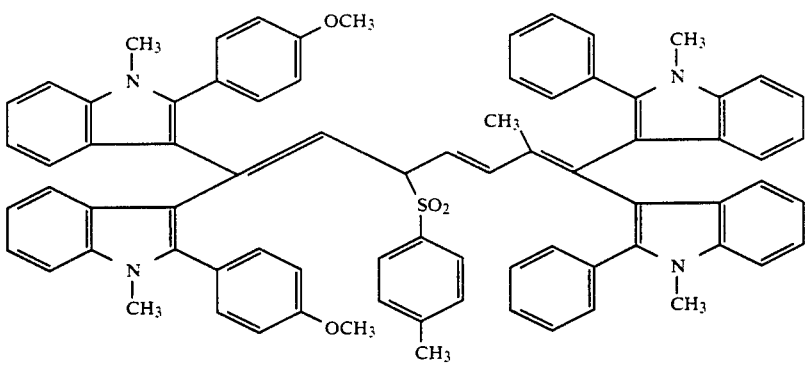

$\lambda_{max}$ in glacial acetic acid: 866 nm.
On acid clay: greenish grey 750–950 nm.

EXAMPLE 77

3 g of the tetraindolylheptamethine derivative of Example 1 are dissolved in a mixture of 40 g of dodecylbenzene and 60 g of chloroparaffin having a 45% Cl content (Marlican from Huls). 223 g of such a solution are mixed with 39.5 g of Desmodur H oxadiazinetrione (NCO content: 20.5%). The iixture is then mixed with 320 g of 0.5% strength polyvinyl alcohol solution and emulsified in the shear gradient of a rotor/stator emulsifier. The emulsion is crosslinked with 76 g of 9.0% strength diethylenetriamine solution. The dispersion is post-treated by warming to 60° C. and stirring at 60° C. for three hours. In this way, a dispersion containing 40% of capsules of capsule size 7.3 μm is obtained.

250 ml of this dispersion are initially introduced and 40 g of finely ground cellulose (Arbocell BE 600/30 from Rettenmeier & Söhne) are slowly sprinkled in with intensive stirring. After at least 30 minutes' intensive stirring, 40 ml of 50% strength SBR latex (Baystal D 1600 from Bayer AG) are added. The resulting 48.5% strength coating composition is diluted with water to a solids content of 30% and coated using an air brush onto the back of a commercial base paper. The add-on after drying is 5 g/m².

The paper thus coated is placed with the coated side on the side of a commercial carbon-free copying paper coated with the developer substance. When pressure is applied to the paper coated with capsules, a grey-blue copy results on the copying paper, which has an intensive absorption in the near infrared region from 750–950 nm.

The other examples can also be used analogously.

EXAMPLE 78

A solution of 2 g of the tetraindolylheptamethine derivative of Example 4 and 3 g of a benzoxazine of the formula

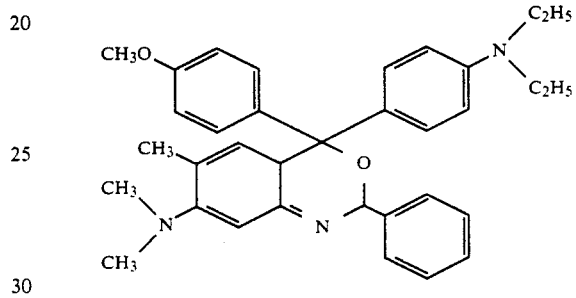

as is described in EP 187,329, in 80 g of diisopropylnaphthalene and 17 g of kerosine is microencapsulated by coacervation in a manner known per se using gelatine and gum arabic, mixed with starch solution and coated on a sheet of paper. This sheet is placed with the coated side on the side of a commercial carbon-free copying paper coated with the developer substance. On exerting pressure on the paper coated with the capsules, an intensive black copy results on the copying paper, which in the near infrared likewise has an intensive absorption from 750–950 nm.

The other examples can also be used analogously.

EXAMPLE 79

32 g of 4,4'-isopropylidene diphenol (bisphenol A), 3.8 g of distearylamide of ethylenediamine, 89 g of kaolin, 20 g of up to 88% hydrolysed polyvinyl alcohol and 55 ml of water are ground in a ball mill until the particle size is about 5 μm. 6 g of the tetraindolylheptamethine derivative of Example 2, 3 g of up to 88% hydrolysed polyvinyl alcohol and 60 ml of water are ground in a 2nd ball mill to a particle size of about 3 μm. The two dispersions are combined and coated onto paper with a dry add-on weight of 5.5 g/m². A greenish grey recording is developed by touching the paper with a heated ballpoint pen, which shows an intensive absorption from 750–950 nm in the near infrared.

The other examples can also be used analogously.

We claim:

1. Tetraindolylheptamethine derivatives of the isomeric formulae

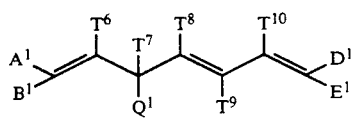

-continued

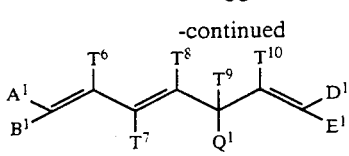

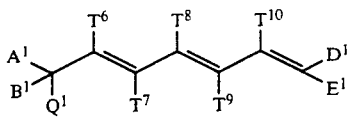

and

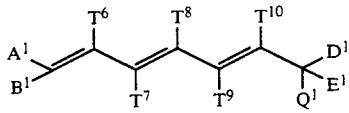

in which $A^1$, $B^1$, $D^1$, and $E^1$ denote

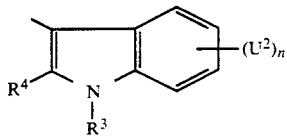

and may be identical to or different from one another,
$Q^1$ denotes

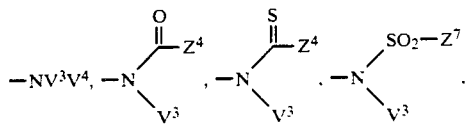

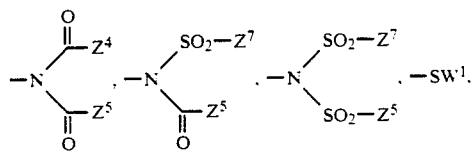

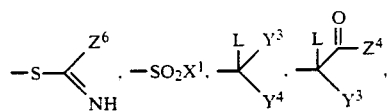

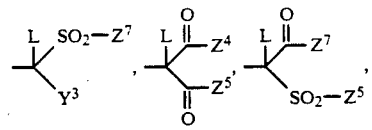

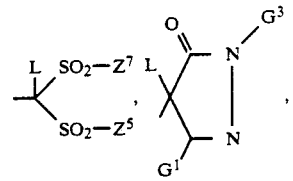

$R^3$ denotes hydrogen, $C_1$-$C_{18}$-alkyl which may be substituted by chlorine, $C_1$-$C_4$-alkoxy, cyano or $C_1$-$C_4$-alkoxycarbonyl, or allyl, cyclopentyl or cyclohexyl, or benzyl, phenethyl, or naphthylmethyl radicals optionally substituted by $C_1$-$C_4$-alkyl, chlorine and/or $C_1$-$C_4$-alkoxy, $R^4$ denotes hydrogen, $C_1$-$C_{18}$-alkyl which may be substituted by chlorine, $C_1$-$C_4$-alkoxy, cyano or $C_1$-$C_4$-alkoxycarbonyl, or allyl, cyclopentyl or cyclohexyl, or benzyl, phenethyl, naphthylmethyl, phenyl, naphthyl, imidazolyl, benzimidiazolyl radicals optionally substituted by $C_1$-$C_4$-alkyl, chlorine, bromine, $C_1$-$C_4$-alkoxy, cyano, nitro and/or $C_1$-$C_4$-alkoxycarbonyl, $T^6$-$T^{10}$ denote hydrogen, $C_1$-$C_8$-alkyl which may be substituted by chlorine, $C_1$-$C_4$-alkoxy, cyano or $C_1$-$C_4$-alkoxycarbonyl, or vinyl, allyl, cyclopentyl, cyclohexyl, fluorine, chlorine, bromine, $C_1$-$C_8$-alkoxy which may be further substituted by $C_1$-$C_4$-alkoxy, or $C_1$-$C_4$-dialkylamino, pyrrolidino, nitro, cyano, $C_1$-$C_4$-alkoxycarbonyl, or benzyl, phenethyl, naphthylmethyl, phenyl, naphthyl, indolyl, indolenyl, imidazolyl or benzimidazolyl radicals optionally substituted by $C_1$-$C_4$-alkyl, chlorine, $C_1$-$C_4$-alkoxy, $C_1$-$C_4$-alkylsulphonyl, cyano and/or $C_1$-$C_4$-alkoxycarbonyl, or in each case two of the radicals $T^6$ to $T^{10}$ denote a bridge of the formulae

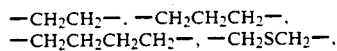

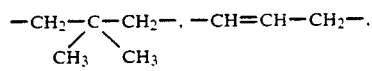

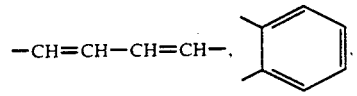

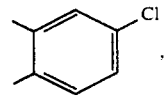

$U^2$ denotes hydrogen, $C_1$-$C_8$-alkyl, allyl, cyclohexyl, benzyl, phenyl, hydroxyl, $C_1$-$C_4$-alkoxy, chlorine, bromine, $C_1$-$C_4$-dialkylamino, nitro, cyano, $C_1$-$C_4$-alkylthio, $C_1$-$C_4$-alkoxycarbonyl, $C_1$-$C_4$-dialkylaminocarbonyl, $C_1$-$C_4$-alkoxycarbonyloxy or $C_1$-$C_4$-alkylsulphonyl or together with $R^3$ denotes a —$CH_2CH_2$— bridge which may be substituted by a maximum of three methyl groups, $V^3$, $V^4$ and $W^1$ independently of one another denote hydrogen, $C_1$-$C_{18}$-alkyl which may be substituted by chlorine, $C_1$-$C_4$-alkoxy, cyano or $C_1$-$C_4$-alkoxycarbonyl, or allyl, cyclopentyl, cyclohexyl or cyano, or benzyl, phenethyl, naphthylmethyl, phenyl, naphthyl, imidazolyl or benzimidazolyl radicals optionally substituted by $C_1$-$C_4$-alkyl, chlorine, bromine, $C_1$-$C_4$-alkoxy, cyano, nitro or $C_1$-$C_4$-alkoxycarbonyl, or $V^3$ and $V^4$ together with the nitrogen atom denote pyrrolidinyl, pyrazolinyl, pyrazolyl or imidazolyl radicals optionally substituted by $C_1$-$C_4$-alkyl, chlorine, $C_1$-$C_4$-alkoxy or phenyl, $X^1$ denotes $C_1$-$C_{18}$-alkyl which may be substituted by chlorine, $C_1$-$C_4$-alkoxy, cyano or $C_1$-$C_4$-alkoxycarbonyl, or allyl, cyclopentyl or cyclohexyl, or benzyl, phenethyl, naphthylmethyl, phenyl, naphthyl or imidazolyl or benzimidazolyl radicals optionally substituted by $C_1$-$C_4$-alkyl, chlorine, bromine, $C_1$-$C_4$-alkoxy, cyano, nitro or $C_1$-$C_4$-alkoxycarbonyl, L denotes hydrogen, $C_1$-$C_8$-alkyl which may be substituted by chlorine, $C_1$-$C_4$-alkoxy, cyano or $C_1$-$C_4$-alkoxycarbonyl, or allyl, cyclopentyl, cyclohexyl, chlorine, cyano or $C_1$-$C_8$-alkoxycarbonyl, or benzyl, phenethyl, phenyl, or naphthyl radicals optionally substituted by $C_1$-$C_4$-alkyl, chlorine, $C_1$-$C_4$-alkoxy, cyano, nitro or $C_1$-$C_4$-alkoxycarbonyl, $Y^3$ and $Y^4$ denote cyano, nitro or phenyl, naphthyl, imidazolyl or benzimidazolyl radicals optionally substituted by $C_1$-$C_4$-alkyl, chlorine, bromine, $C_1$-$C_4$-alkoxy, cyano, nitro, $C_1$-$C_4$-alkylsulphonyl or $C_1$-$C_4$-alkoxycarbonyl, $Z^4$, $Z^5$, $Z^6$ and $Z^7$ independently of one another denote hydrogen, $C_1$-$C_{18}$-alkyl which may be substituted by chlorine, $C_1$-$C_4$-alkoxy, cyano or $C_1$-$C_4$-alkoxycarbonyl, or allyl, cyclopentyl, cyclohexyl, $C_1$-$C_{18}$-alkoxy, $C_1$-$C_{18}$-alkylthio, cyclopentoxy, cyclohexoxy, amino or mono- or bis-$C_1$-$C_{12}$-alkylamino, or anilino, N-$C_1$-$C_4$-alkylanilino, diphenylamino, benzyl, benzyloxy, benzylamino, N-$C_1$-$C_4$-alkylbenzylamino, dibenzylamino, phenethyl, phenethoxy, phenethamino, phenyl, naphthyl, imidazolyl or benzimidazolyl radicals optionally substituted by $C_1$-$C_4$-alkyl, chlorine, bromine, $C_1$-$C_4$-alkoxy, cyano, nitro or $C_1$-$C_4$-alkoxycarbonyl, or $Z^4$ together with $Z^5$ denote a bridge of the formulae

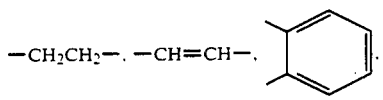

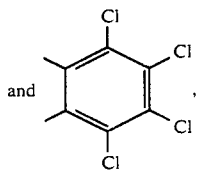

$Z^4$ together with $V^3$ or $Y^3$ denote a bridge of the formulae

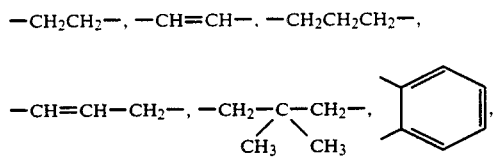

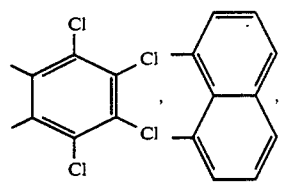

$G^1$ denotes hydrogen, $C_1$-$C_8$-alkyl which may be substituted by chlorine, $C_1$-$C_4$-alkoxy, cyano or $C_1$-$C_4$-alkoxycarbonyl, or allyl, cyclopentyl, cyclohexyl, hydroxyl, chlorine, $C_1$-$C_8$-alkoxy, cyano, $C_1$-$C_8$-alkoxycarbonyl, nitro or $C_1$-$C_8$-alkylsulphonyl, or benzyl, phenethyl, phenyl, naphthyl, imidazolyl or benzimidazolyl radicals optionally substituted by $C_1$-$C_4$-alkyl, chlorine, $C_1$-$C_4$-alkoxy, cyano, nitro or $C_1$-$C_4$-alkoxycarbonyl, $G^3$ denotes hydrogen, $C_1$-$C_8$-alkyl which may be substituted by chlorine, $C_1$-$C_4$-alkoxy, cyano or $C_1$-$C_4$-alkoxycarbonyl, or allyl, cyclopentyl or cyclohexyl, or benzyl, phenethyl, phenyl, or naphthyl radicals optionally substituted by $C_1$-$C_4$-alkyl, chlorine, $C_1$-$C_4$-alkoxy, cyano, nitro or $C_1$-$C_4$-alkoxycarbonyl, and n denotes 1 or 2.

2. Tetraindoylheptamethine derivative according to claim in, in which $Q^1$ denotes $C_1$-$C_8$-mono- or dialkylamine, or pyrrolidino, pyrazolo, or imidazolo radicals optionally substituted by methyl, chlorine or methoxy, or anilino, N-$C_1$-$C_4$-alkylanilino, diphenylamino, benzylamino, N-$C_1$-$C_4$-alkyl-N-benzylamino, benzoylamino, N-$C_1$-$C_4$-alkylbenzoylamino, N-phenylbenzoylamino, benzenesulphonylamino, N-$C_1$-$C_4$-alkylbenzenesulphonylamino, phthalimido, naphthalimido, homophthalimido, benzoyl-2-sulphonylimido, succinimido or maleimido radicals optionally substituted by methyl, ethyl, chlorine, cyano or nitro, or aminocarbonylamino, $C_1$-$C_8$-alkoxycarbonylamino or $C_1$-$C_8$-alkylthio, or phenylthio,

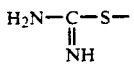

or $C_1$-$C_8$-alkylsulphonyl optionally substituted by methyl, chlorine or methoxy, phenylsulphonyl, benzylsulphonyl or naphthylsulphonyl optionally substituted by methyl, ethyl, chlorine, bromine, cyano or methoxycarbonyl, or benzyl, naphthylmethyl, imidazolylmethyl, or benzimidazolylmethyl radicals substituted in the α-position by cyano, $C_1$-$C_4$-alkoxycarbonyl, $C_1$-$C_4$-alkylsulphonyl, $C_1$-$C_4$-alkanoyl or benzoyl and optionally furthermore substituted by methyl, ethyl, chlorine, bromine, cyano, nitro or methoxycarbonyl, or dicyanomethyl, cyano-$C_1$-$C_4$-alkoxycarbonylmethyl, bis-$C_1$-$C_4$-alkoxycarbonylmethyl, cyano-$C_1$-$C_4$-alkanoylmethyl or bis-$C_1$-$C_4$-alkanoylmethyl, or cyanobenzoylmethyl, $C_1$-$C_4$-alkanoyl-benzoylmethyl, $C_1$-$C_4$-alkoxycarbonylbenzoylmethyl, dibenzoylmethyl, cyanophenylsulphonylmethyl, $C_1$-$C_4$-alkanoyl-phenylsulphonylmethyl, $C_1$-$C_4$-alkoxycarbonylphenylsulphonylmethyl or bisphenylsulphonylmethyl radicals optionally substituted by methyl, ethyl, chlorine, cyano, nitro or methoxycarbonyl, or the radicals of 1,3-cyclopentanedione, 1,3-cyclohexanedione, 1,3-indanedione, Meldrum's acid, pyrazolone optionally substituted by methyl, ethyl, chlorine, methoxy, ethoxy, phenyl, cyano, methoxycarbonyl or ethoxycarbonyl, $R^3$ denotes hydrogen, $C_1$-$C_8$-alkyl which may be substituted by chlorine, methoxy, ethoxy, cyano or methoxycarbonyl, or allyl, cyclopentyl or cyclohexyl, or benzyl, or phenethyl radicals optionally substituted by methyl, chlorine or methoxy, $R^4$ denotes hydrogen, $C_1$-$C_8$-alkyl which may be substituted by chlorine, methoxy, ethoxy, cyano or methoxycarbonyl, or allyl, cyclopentyl or cyclohexyl, or benzyl, phenethyl, phenyl, naphthyl, or benzimidazolyl radicals optionally subsituted by methyl, chlorine, methoxy, cyano, nitro and/or methoxycarbonyl, $T^6$ and $T^{10}$ denote hydrogen, $C_1$–$C_8$-alkyl which may be substituted by chlorine, methoxy, cyano or methoxycarbonyl, or vinyl allyl, cyclopentyl, cyclohexyl, chlorine, $C_1$–$C_8$-alkoxy, cyano, methoxycarbonyl, nitro or benzyl, or phenyl radicals optionally substituted by methyl, chlorine, cyano or methoxy, $T^7$ to $T^9$ denote hydrogen, $C_1$–$C_8$-alkyl which may be substituted by chlorine, methoxy, cyano or methoxycarbonyl, or allyl, cyclopentyl, cyclohexyl, chlorine, bromine, cyano, methoxycarbonyl or ethoxycarbonyl, nitro, $C_1$–$C_4$-alkoxy, $C_1$–$C_4$-dialkylamino or benzyl, or phenyl, naphthyl, or indolenyl, imidazolyl, or benzimidazolyl, radicals optionally substituted by methyl, ethyl, chlorine, methoxy, ethoxy, cyano, nitro and/or methoxycarbonyl, or $T^7$ together with $T^8$ or $T^9$ or $T^8$ together with $T^9$ denote a bridge of the formulae

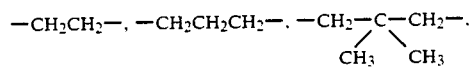

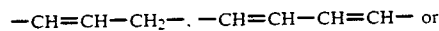

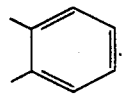

$Q^2$ denotes hydrogen, $C_1$–$C_4$-alkyl, cyclohexyl, benzyl, $C_1$–$C_4$-alkoxy, chlorine, $C_1$–$C_4$-dialkylamino, nitro, cyano, methoxycarbonyl or ethoxycarbonyl or methylsulphonyl, where $U^2$ may be in the 5-, 6- and/or 7-position of the indolyl radical, or a radical $U^2$ in the 7-position together with $R^3$ can form a bridge of the formulae

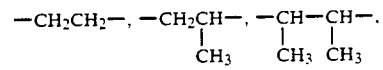

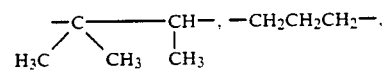

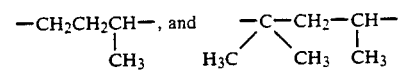

n denotes 1 or 2.

3. Tetraindolylheptamethine derivative according to claim 1, in which $A^1$, $B^1$, $D^1$ and $E^1$ denote

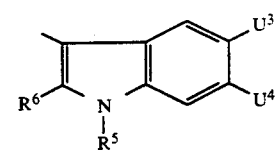

$Q^1$ denotes dimethylamino, diethylamino, dipropylamino, dibutylamino, propylamino, butylamino, pyrrolidino, pyrazolo, imidazolo, anilino, 4-methylanilino, 4-chloroanilino, 4-methoxyanilino, 4-nitroanilino, N-methylanilino, benzylamino, N-methylbenzylamino, N-ethylbenzylamino, benzoylamino, benzenesulphonylamino, phthalimido, naphthalimido, succinimido, maleiimido, methylthio, ethylthio, phenylthio, methylsulphonyl, ethylsulphonyl, propylsulphonyl, butylsulphonyl, hexylsulphonyl, octylsulphonyl, benzenesulphonyl, 4-methylbenzenesulphonyl, 4-chlorobenzenesulphonyl, α-cyanobenzyl, α-cyanobenzyl, α-cyano-4-methylbenzyl, α-cyano-4-chlorobenzyl, α-cyano-4-nitrobenzyl, dicyanomethyl, cyanomethoxycarbonylmethyl, cyanoethoxycarbonylmethyl, bismethoxycarbonylmethyl, bis-ethoxycarbonylmethyl, 1-cyanoaceton-1-yl, 1-cyanobutanon-1-yl, 1-methoxycarbonylaceton-1-yl, 1-ethoxycarbonylaceton-1-yl, 1,3-pentanedion-3-yl, 1-benzoylaceton-1-yl, 2-cyano-1-phenylethanon-2-yl, 2-methoxycarbonyl-1-phenylethanon-2-yl, dibenzoylmethyl, cyanophenylsulphonylmethyl, bisphenylsulphonylmethyl, 1,3-cyclopentanedion-2-yl, 1,3-cyclohexanedion-2-yl, 5,5-dimethyl-1,3-cyclohexanedion-2-yl, 1,3-indanedion-2-yl, 2,2-dimethylperhydro-1,3-dioxine-4,6-dion-5-yl, 3-methyl-1-phenyl-2-pyrazolin-5-on-4-yl, 1-(2-chlorophenyl)-3-methyl-2-pyrazolin-5-on-4-yl, 3-methyl-1-(4-methylphenyl)-2-pyrazolin-5-on-4-yl, 3-methyl-1-(4-nitrophenyl)-2-pyrazolin-5-on-4-yl, 3-methyl-1-phenyl-5-imino-2-pyrazolin-4-yl, 3-methyl-1-(3-sulpholanyl)-2-pyrazolin-5-on-4-yl, 3-ethoxycarbonyl-1-phenyl-2-pyrazolin-5-on-4-yl, or 3-aminocarbonyl-1-phenyl-2-pyrazolin-5-on-4-yl, $R^5$ denotes methyl, ethyl, propyl, butyl, hexyl, octyl, 2-cyanoethyl, 2-methoxyethyl, 2-methoxycarbonylethyl, 2-chloroethyl, 2-acetoxyethyl, cyclohexyl, allyl or benzyl, $R^6$ denotes methyl, ethyl, propyl, butyl, hexyl, octyl, cyclohexyl, benzyl, phenyl, 2-, 3- or 4-chlorophenyl, 2-, 3- or 4-methoxyphenyl, 4-nitrophenyl, 2,4-dichlorophenyl, or 2-, 3- or 4-tolyl, $T^6$ and $T^{10}$ independently denote hydrogen, methyl, ethyl, propyl, butyl, vinyl, 2-chloroethyl, 2-cyanoethyl, chlorine, cyano, phenyl, 4-tolyl or 4-chlorophenyl, $T^7$ and $T^9$ independently denote hydrogen, methyl, ethyl, propyl, butyl, chlorine, cyano, methoxycarbonyl, dimethylamino, phenyl, 4-tolyl, 4-chlorophenyl, or $R^7$ and $T^9$ together denote a grouping of the formulae

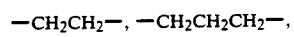

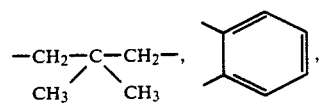

$T^8$ denotes hydrogen, methyl, ethyl, propyl, butyl, chlorine, bromine, cyano, phenyl, 4-tolyl, 4-chlorophenyl, 4-nitrophenyl, 3,3-dimethyl-indolen-2-yl, or 2-benzimidazolyl, and $U^3$ and $U^4$ denote hydrogen, methyl, methoxy, chlorine, cyano, methoxycarbonyl or nitro.

4. The tetraindolylheptamethine derivative according to claim 1, having the formula

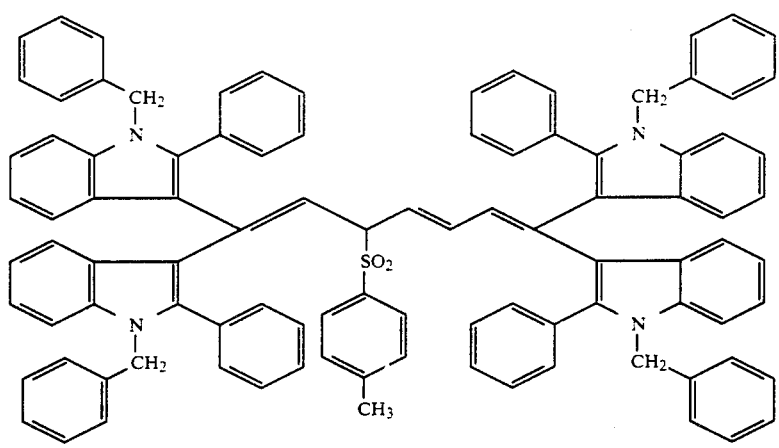

UNITED STATES PATENT AND TRADEMARK OFFICE
CERTIFICATE OF CORRECTION

PATENT NO. : 5,118,814
DATED : June 2, 1992
INVENTOR(S) : Horst Berneth, et al.

It is certified that error appears in the above-identified patent and that said Letters Patent is hereby corrected as shown below:

Col. 24, Line 45        End of line delete "run" and substitute --nm--.

Signed and Sealed this

Twenty-first Day of September, 1993

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,118,814
DATED : June 2, 1992
INVENTOR(S) : Horst Berneth, et. al.

It is certified that error appears in the above-indentified patent and that said Letters Patent is hereby corrected as shown below:

Column 24, line 45, delete "run" and substitute --nm--.

Signed and Sealed this

Ninth Day of November, 1993

*Attest:*

BRUCE LEHMAN

*Attesting Officer*      *Commissioner of Patents and Trademarks*